US008753466B2

(12) United States Patent
Thorson

(10) Patent No.: US 8,753,466 B2
(45) Date of Patent: Jun. 17, 2014

(54) METHOD OF MAKING DISPOSABLE ABSORBENT GARMENTS EMPLOYING ELASTOMERIC FILM LAMINATE BODY PANELS

(75) Inventor: Russell E. Thorson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 606 days.

(21) Appl. No.: 12/605,092

(22) Filed: Oct. 23, 2009

(65) Prior Publication Data

US 2011/0094661 A1    Apr. 28, 2011

(51) Int. Cl.
*A61F 13/49* (2006.01)

(52) U.S. Cl.
USPC ........... 156/177; 156/204; 156/267; 156/269; 604/385.21

(58) Field of Classification Search
None
See application file for complete search history.

(56) References Cited

U.S. PATENT DOCUMENTS

| | | | |
|---|---|---|---|
| 5,660,657 A | 8/1997 | Rajala et al. | |
| 5,711,832 A * | 1/1998 | Glaug et al. | 156/73.1 |
| 6,312,420 B1 | 11/2001 | Sasaki et al. | |
| 6,702,798 B2 | 3/2004 | Christoffel et al. | |
| 7,118,558 B2 * | 10/2006 | Wu et al. | 604/385.29 |
| 7,727,207 B2 | 6/2010 | Erdman | |
| 2002/0147439 A1 * | 10/2002 | Tanaka et al. | 604/398 |
| 2003/0100876 A1 | 5/2003 | Molee | |
| 2004/0243089 A1 | 12/2004 | Veith et al. | |
| 2008/0071240 A1 | 3/2008 | Erdman et al. | |
| 2008/0287897 A1 | 11/2008 | Reyes et al. | |
| 2009/0088719 A1 | 4/2009 | Driskell | |
| 2009/0187157 A1 | 7/2009 | Hornung et al. | |
| 2010/0059168 A1 * | 3/2010 | Endo et al. | 156/164 |

FOREIGN PATENT DOCUMENTS

| | | |
|---|---|---|
| EP | 2 087 871 A1 | 8/2009 |
| KR | 10-0235519 B1 | 12/1999 |
| KR | 10-0245353 B1 | 2/2000 |
| WO | WO 93/09746 A1 | 5/1993 |
| WO | WO 94/00292 A1 | 1/1994 |
| WO | WO 97/30671 A2 | 8/1997 |
| WO | WO 01/13748 A1 | 3/2001 |
| WO | WO 01/13850 A1 | 3/2001 |
| WO | WO 01/45613 A1 | 6/2001 |
| WO | WO 2004/093765 A1 | 11/2004 |
| WO | WO 2007/099493 A1 | 9/2007 |
| WO | WO 2007133127 A1 * | 11/2007 |
| WO | WO 2008123310 A1 * | 10/2008 |
| WO | WO 2009/031592 A1 | 3/2009 |
| WO | WO 2009/064224 A1 | 5/2009 |
| WO | WO 2009/064225 A1 | 5/2009 |
| WO | WO 2011/064995 A1 | 6/2011 |

* cited by examiner

*Primary Examiner* — Barbara J Musser
(74) *Attorney, Agent, or Firm* — Kimberly-Clark Worldwide, Inc.

(57) ABSTRACT

In one embodiment, a method of making disposable absorbent garments includes providing an outer cover web having front and back waist edges; attaching elastomeric front and back body panel webs to the outer cover web. The front and back body panel webs comprise an elastomeric film laminate. Portions of the outer cover web are removed to define a series of spaced apart holes. The elastomeric front body panel web defines a front body panel web width that extends at least 50% of a shortest distance extending from the front waist edge to each hole, and the elastomeric back body panel web defines a back body panel width that extends at least 50% of a shortest distance extending from the back waist edge to each hole.

12 Claims, 17 Drawing Sheets

METHOD OF MAKING DISPOSABLE ABSORBENT GARMENTS EMPLOYING ELASTOMERIC FILM LAMINATE BODY PANELS

BACKGROUND

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products. With certain products, such as adult incontinence underwear and enuresis pants, it is important that the garment feel as much as possible like "regular" underwear to promote an improved sense of normalcy to the wearer who suffers from incontinence or enuresis. Many conventional pant-like, pull-on style absorbent garments currently on the market, such as that depicted in FIG. 1, employ a product chassis in which multiple threads of elastic are sandwiched between two nonwoven fabric layers. The strands extend around the body, such that the elastic forces extend primarily around the wearer's waist, as is the case with traditional cloth briefs. This design can provide good fit and leakage performance, but has the potential to be further improved in terms of looking and feeling even more like "regular" cloth underwear.

One class of materials that offers the potential to make absorbent garments more "underwear-like" is that of elastomeric film laminates. Elastomeric film laminates are typically elastomeric films sandwiched between two nonwoven fabric layers. The films provide elastic properties similar to elastic threads, but offer a smoother, more uniform appearance. Some products currently on the market employ such elastomeric laminates, and utilize a "three-piece" pant construction in which front and back body panels are each constructed of an elastomeric film laminate and are connected together via an absorbent insert that extends between them. Such designs, however, can in certain instances introduce a number of drawbacks.

First, many disposable absorbent underwear machines currently in operation in the industry employ a "one-piece" approach to forming the product chassis, in which a "full-length" outer cover layer is formed before the absorbent insert is attached. After the full-length outer cover layer is present in the process, front and back panels are superposed atop the outer cover layer, and elastic threads are sandwiched between the front panel and the outer cover layer, and between the back panel and the outer cover layer. These large and expensive machines are configured primarily to make these "one-piece" pant configurations, and modifying the machines to allow them to make "three-piece" pant configurations would be an expensive, complicated, and time-consuming undertaking. As a result, the "three-piece" pants currently on the market that employ desirable elastomeric films cannot be readily produced on existing "one-piece" pant manufacturing assets. Accordingly, a solution is needed to allow manufacturers to employ existing "one-piece" pant manufacturing assets to produce more underwear-like garments that employ elastomeric film laminates.

Second, certain "three-piece" designs currently on the market that employ elastomeric films suffer from a notable deficiency. The design of certain products results in a region of the pant that is not particularly "underwear-like." Specifically, a region longitudinally between an elasticized waist panel and an elasticized leg edge is devoid of contracting force, and this region tends to bunch and billow during wear. Such billowing and puffing is undesirable for the consumer, as such condition can impact the discretion of the product, as well as negatively affect the fit and aesthetic aspects of the garment.

Therefore, there is a need for improved absorbent garment designs that are compatible with existing manufacturing assets in the industry. Furthermore, there is a need for improved designs of absorbent garments that employ elastomeric film laminates. Finally, there is a need for manufacturing techniques that utilize existing manufacturing capabilities but that provide improved, more underwear-like absorbent garments.

SUMMARY OF THE INVENTION

In response to the aforementioned needs, a new method for making disposable absorbent garments has been invented. In one embodiment, the method comprises providing an outer cover web traveling in a machine direction, the outer cover web having a front waist edge and a back waist edge, both the front waist edge and the back waist edge extending in the machine direction. The embodiment further comprises providing an elastomeric front body panel web traveling in the machine direction, superposing the elastomeric front body panel web on the outer cover web, and attaching the front body panel web to the outer cover web, the front body panel web comprising an elastomeric film laminate. The embodiment further comprises providing an elastomeric back body panel web traveling in the machine direction, superposing the elastomeric back body panel web on the outer cover web, and attaching the back body panel web to the outer cover web, the back body panel web comprising an elastomeric film laminate. The outer cover web, the front body panel web, and the back body panel web collectively define a composite garment web. The embodiment further comprises providing a supply of individual absorbent assemblies, superposing individual absorbent assemblies over the composite garment web, and attaching the individual absorbent assemblies to the composite garment web. The embodiment further comprises removing portions of the outer cover web to define a series of spaced apart holes, thereby defining in the composite garment web a series of interconnected disposable absorbent garments. The elastomeric front body panel web defines a front body panel web width that extends in a cross-machine direction, and the front body panel web width extends at least 50% of a shortest distance extending from the front waist edge to each hole. Similarly, the elastomeric back body panel web defines a back body panel width that extends in a cross-machine direction, and the back body panel web width extends at least 50% of a shortest distance extending from the back waist edge to each hole. The embodiment further comprises folding the composite garment web along a central fold line that extends in the machine direction, such that the front waist edge is brought into close proximity with the back waist edge. The embodiment further comprises attaching the front body panel web to the back body panel web to create a series of side seam bonds spaced apart in the machine direction. The embodiment further comprises cutting the composite garment web at a series of cut locations spaced apart in the machine direction to create the plurality of disposable absorbent garments.

In another embodiment, the method comprises providing an outer cover web traveling in a machine direction, the outer cover web having a front waist edge and a back waist edge, both the front waist edge and the back waist edge extending in the machine direction. The embodiment further comprises attaching a front leg elastic member to the outer cover web, the front leg elastic member traveling predominantly in the machine direction. The embodiment further comprises attaching a continuous back leg elastic member to the outer cover web, the back leg elastic member traveling predominantly in the machine direction. The embodiment further comprises providing an elastomeric front body panel web traveling in the machine direction, superposing the elastomeric front body panel web on the outer cover web, and attaching the front body panel web to the outer cover web, the front body panel web comprising an elastomeric film laminate. The embodiment further comprises providing an elastomeric back body panel web traveling in the machine direction, superposing the elastomeric back body panel web on the outer cover web, and attaching the back body panel web to the outer cover web, the back body panel web comprising an elastomeric film laminate. In this embodiment, the front body panel web comprises an elastomeric film layer and a nonwoven layer, and attaching the front body panel web to the outer cover web comprises adhering the elastomeric film layer of the front body panel web directly to the outer cover web. Further, the back body panel web comprises an elastomeric film layer and a nonwoven layer, and attaching the back body panel web to the outer cover web comprises adhering the elastomeric film layer of the back body panel web directly to the outer cover web. After attaching the front body panel web to the outer cover web and after attaching the back body panel web to the outer cover web, the front body panel web is spaced in the cross-machine direction apart from the back body panel web. The outer cover web, the front body panel web, and the back body panel web collectively define a composite garment web. The embodiment further comprises providing a supply of individual absorbent assemblies, superposing individual absorbent assemblies over the composite garment web, and attaching the individual absorbent assemblies to the composite garment web, wherein at least a portion of each individual absorbent assembly overlays at least a portion of the elastomeric front body panel web and wherein at least a portion of each individual absorbent assembly overlays at least a portion of the elastomeric back body panel web. The embodiment further comprises removing portions of the outer cover web to define a series of spaced apart holes, thereby defining in the composite garment web a series of interconnected disposable absorbent garments. The elastomeric front body panel web defines a front body panel web width that extends in a cross-machine direction, the front body panel web width extending at least 90% of a shortest distance extending from the front waist edge to each hole. The elastomeric back body panel web defines a back body panel width that extends in a cross-machine direction, the back body panel web width extending at least 90% of a shortest distance extending from the back waist edge to each hole. The embodiment further comprises folding the composite garment web along a central fold line that extends in the machine direction, such that the front waist edge is brought into close proximity with the back waist edge. The embodiment further comprises attaching the front body panel web to the back body panel web to create a series of side seam bonds spaced apart in the machine direction. The embodiment further comprises cutting the composite garment web at a series of cut locations spaced apart in the machine direction to create the plurality of disposable absorbent garments.

DEFINITIONS

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least percent of its relaxed length and which will recover, upon release of the applied force, at least 20 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction when the article is in a fully stretched and laid-flat condition, prior to the joining of the side seams.

"Member" when used in the singular can have the dual meaning of a single element or a plurality of elements.

These terms may be defined with additional language in the remaining portions of the specification.

DETAILED DESCRIPTION OF EXEMPLARY EMBODIMENTS

Figure 1:
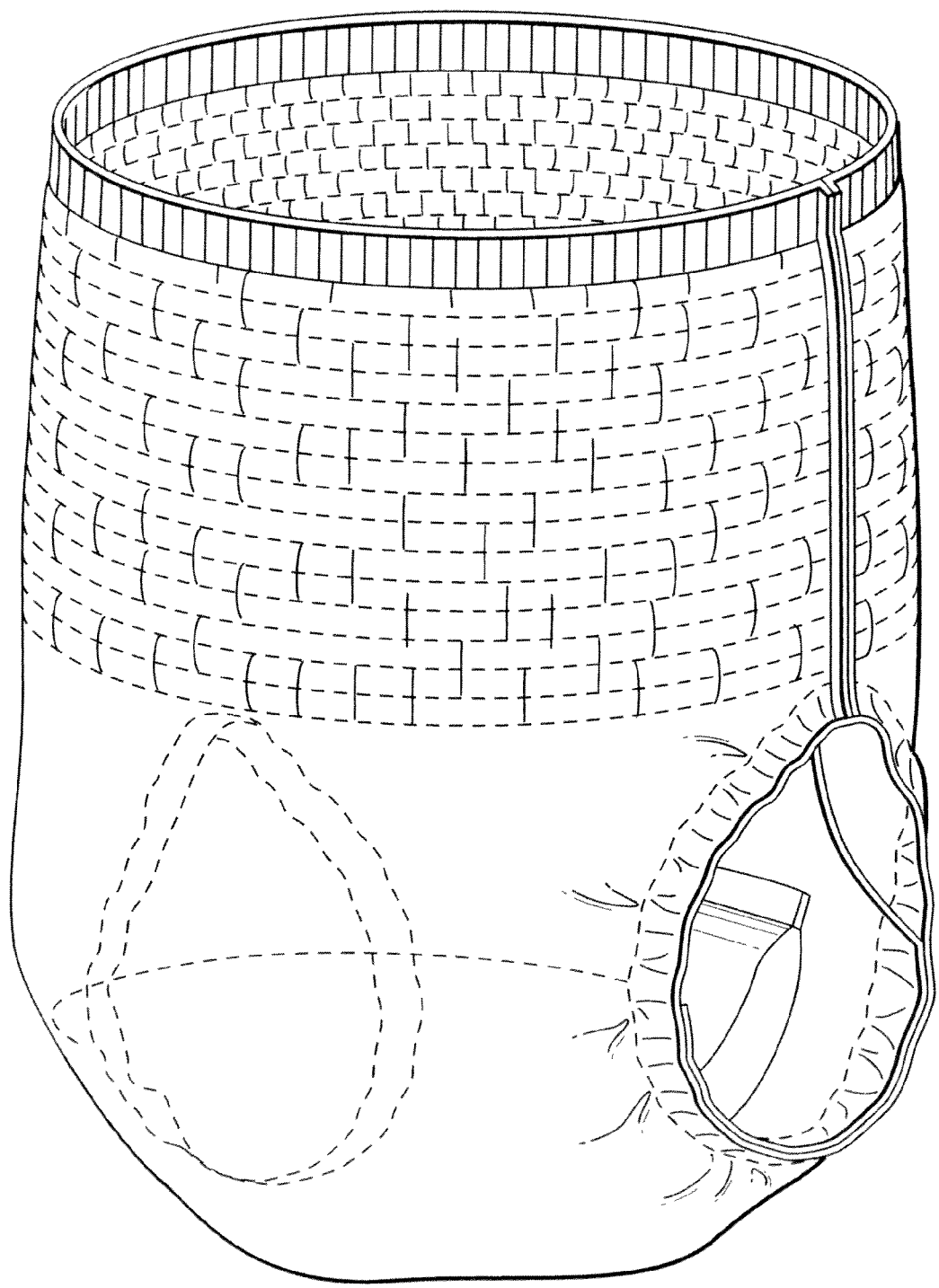
FIG. 1 representatively illustrates a perspective view of a conventional disposable absorbent garment.
Figure 2:
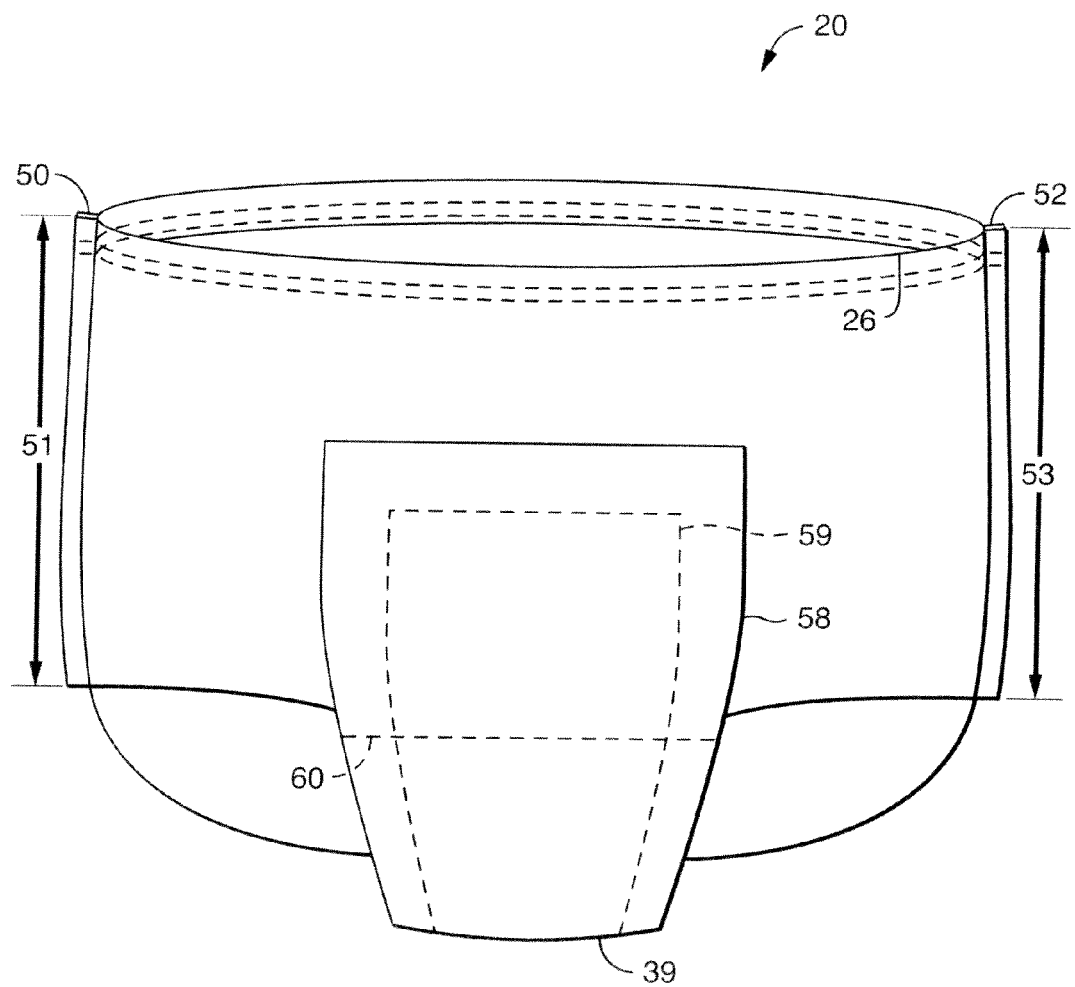
FIG. 2 representatively illustrates a front perspective view of a disposable absorbent article incorporating principles of the present invention.
Figure 3:
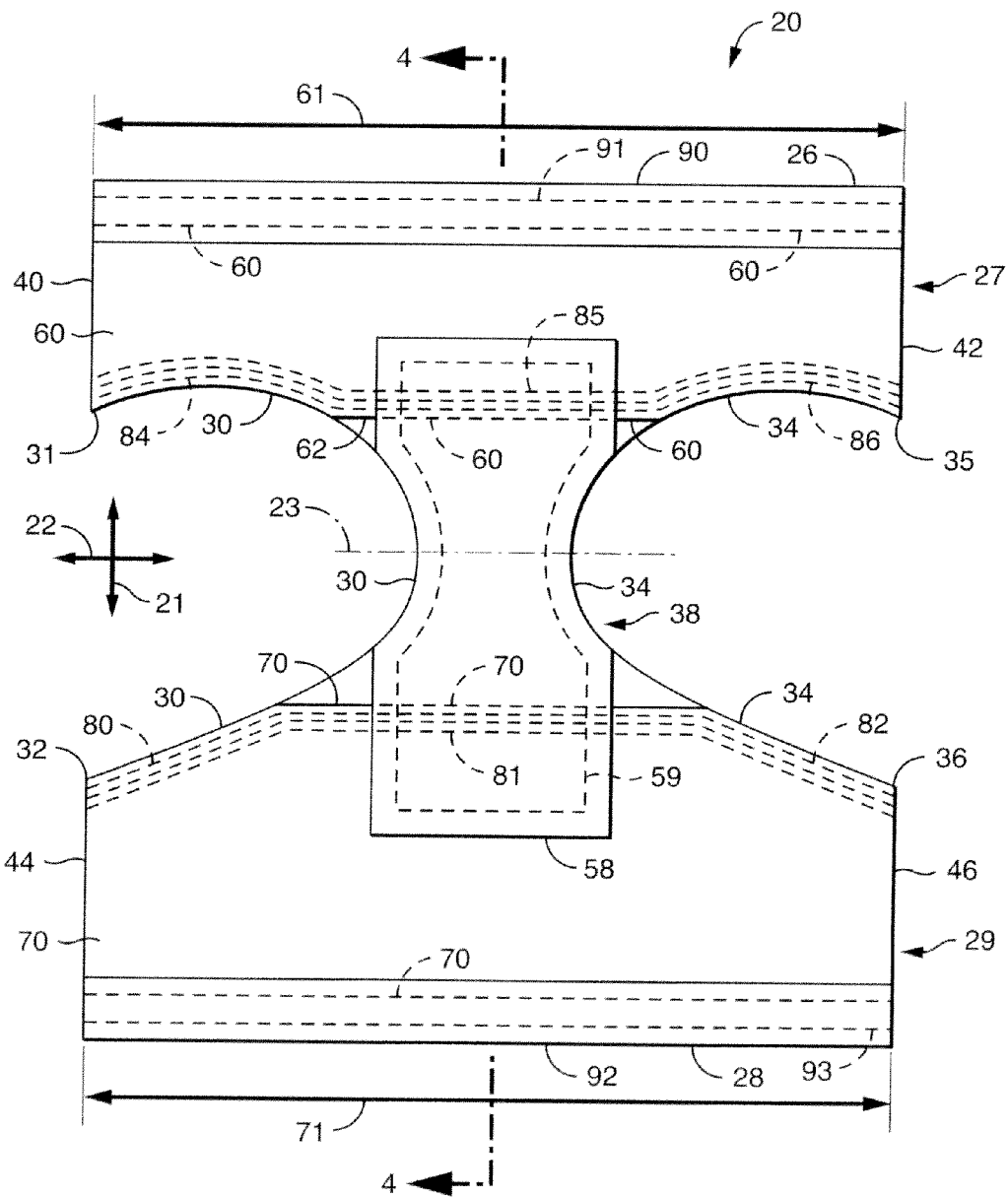
FIG. 3 representatively illustrates a plan view of a disposable absorbent article incorporating principles of the present invention, shown in a longitudinally stretched and laid-flat condition, prior to the joining of the front and back waist regions, and showing the surface of the article that faces toward the wearer when the article is worn.
Figure 4:
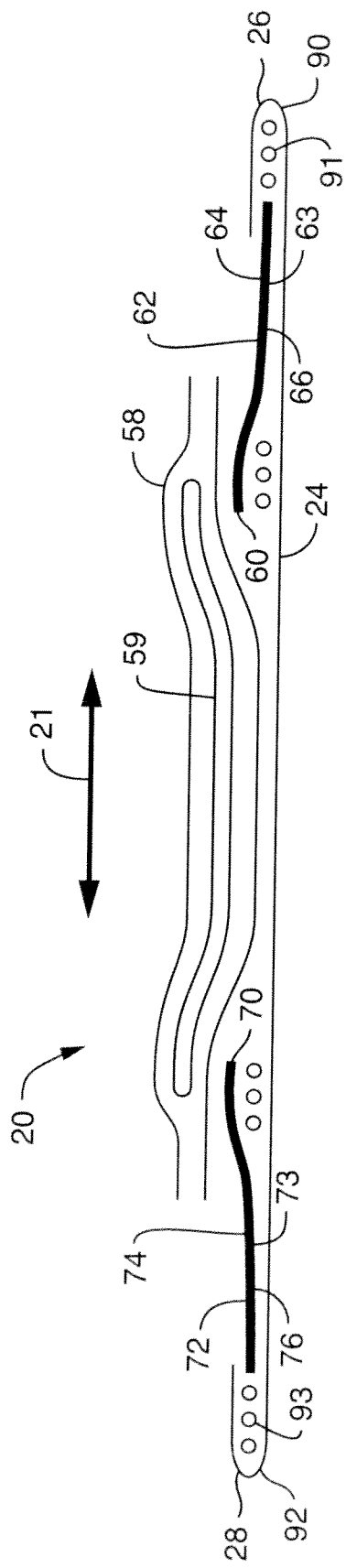
FIG. 4 is a cross-sectional view of the article of FIG. 3 as viewed along line 4-4.
Figure 5:
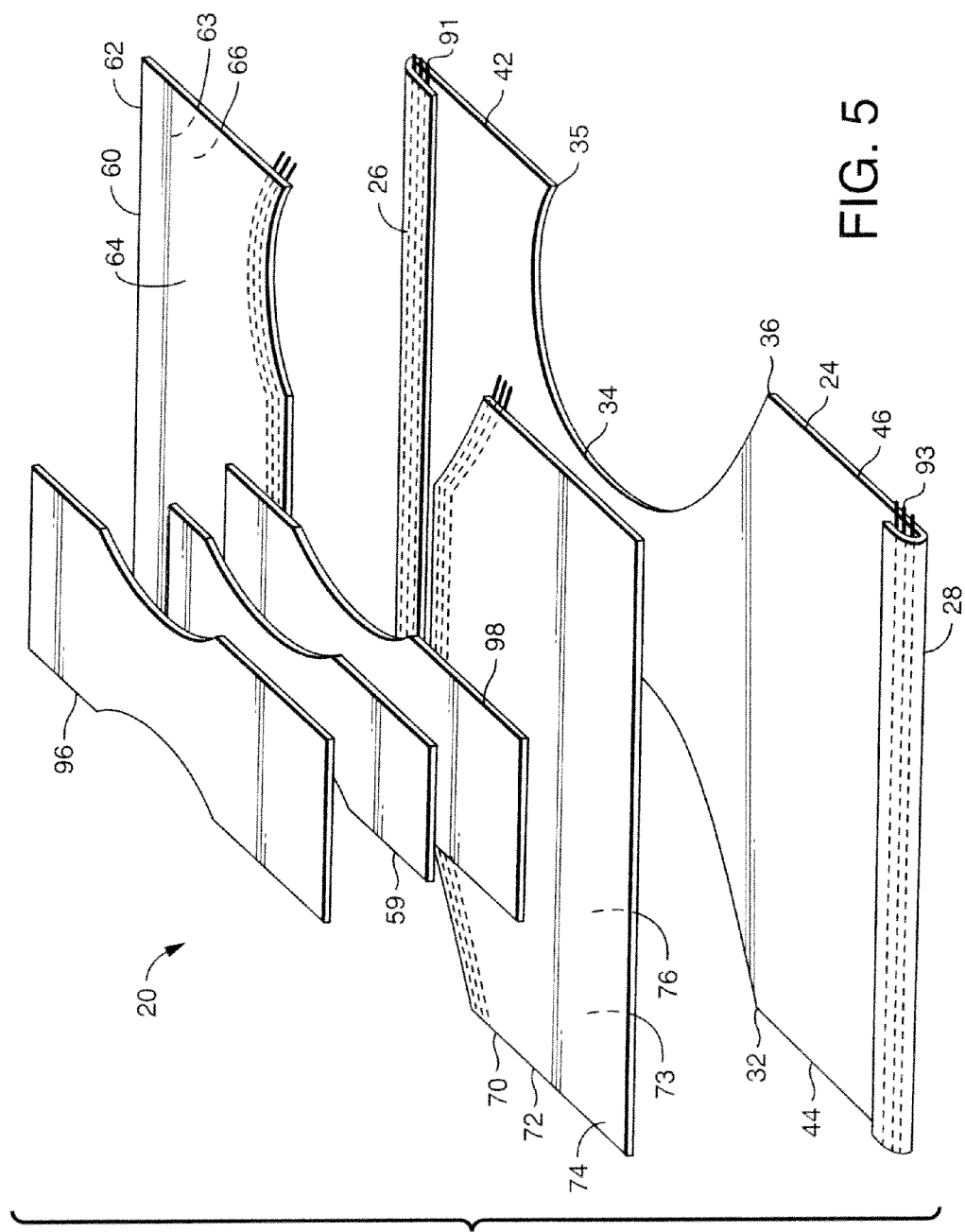
FIG. 5 is an exploded view of the article of FIGS. 3 and 4.
Figure 6:
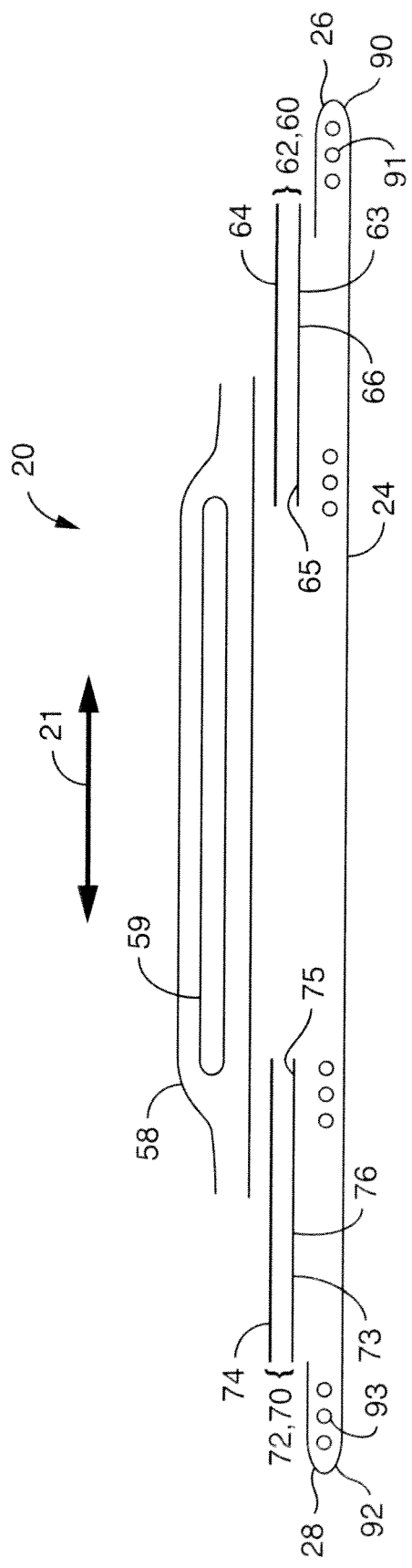
FIG. 6 is a cross-sectional view of an alternative embodiment of the article of FIG. 3 as viewed along line 4-4.
Figure 7:
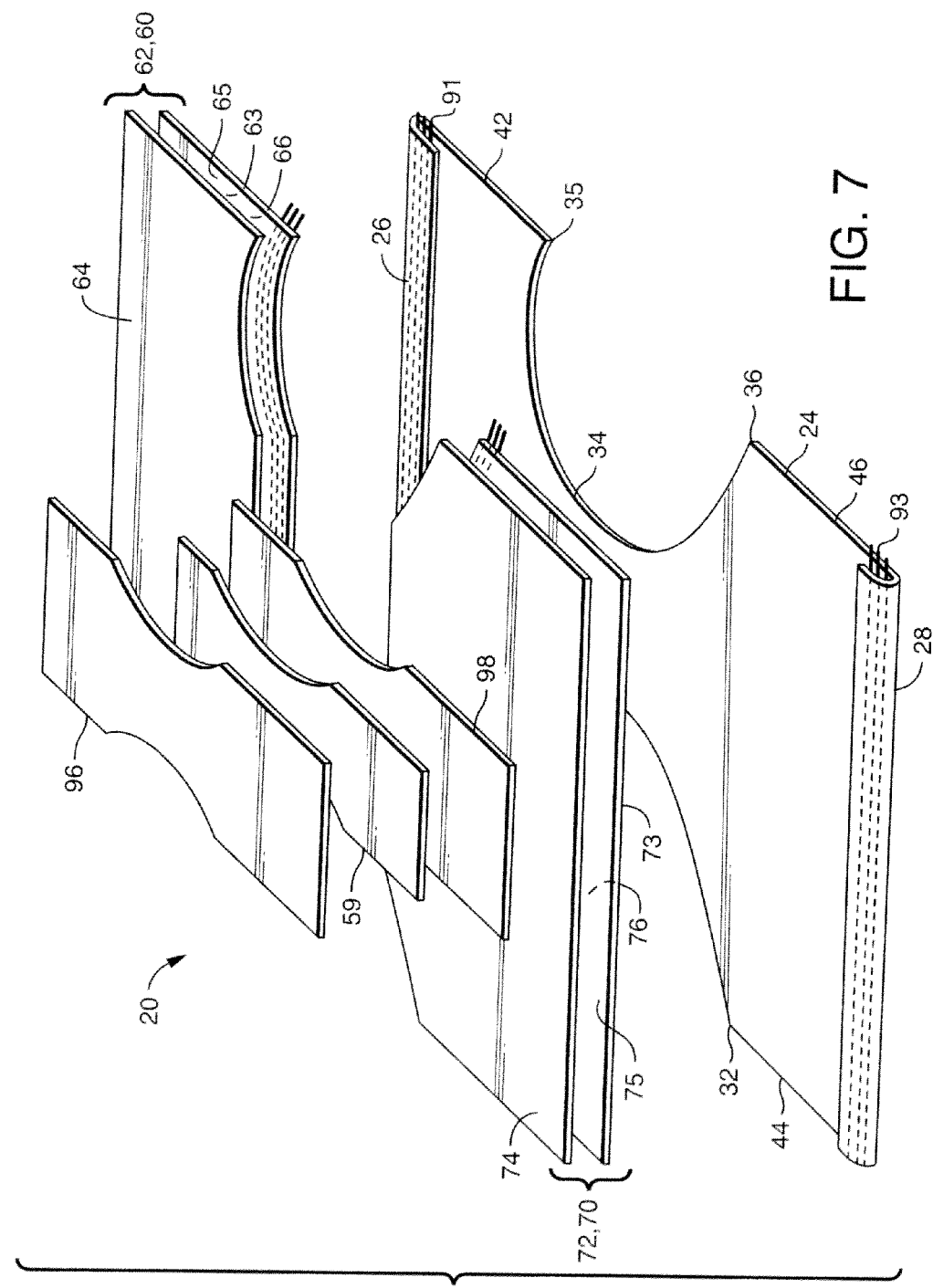
FIG. 7 is an exploded view of the article of FIG. 6.
Figure 8:
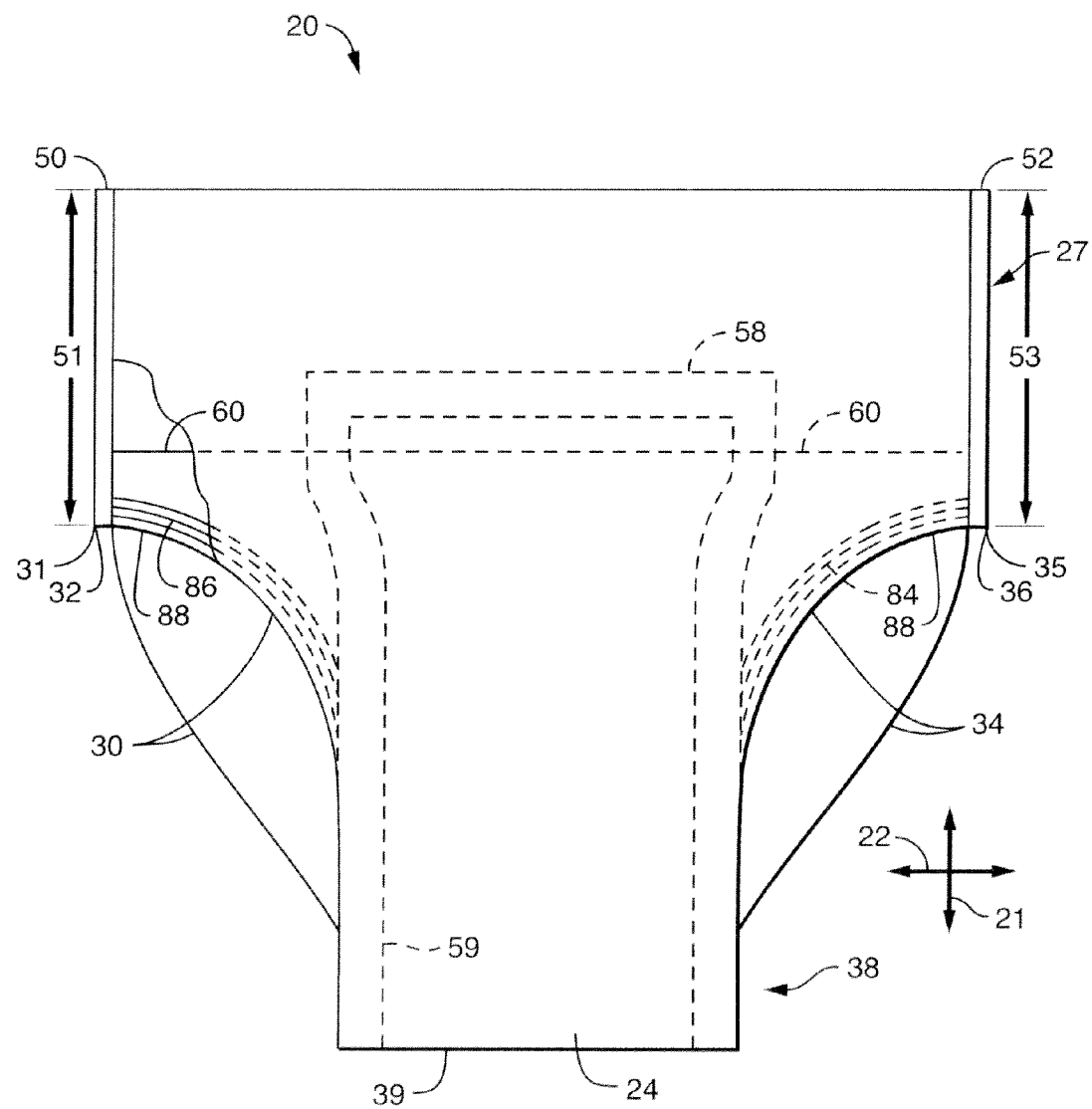
FIG. 8 representatively illustrates a front plan view of a disposable absorbent article incorporating principles of the present invention, shown in a fully assembled, longitudinally stretched, and laid-flat condition, and with portions cut away to show underlying features.
Figure 9:
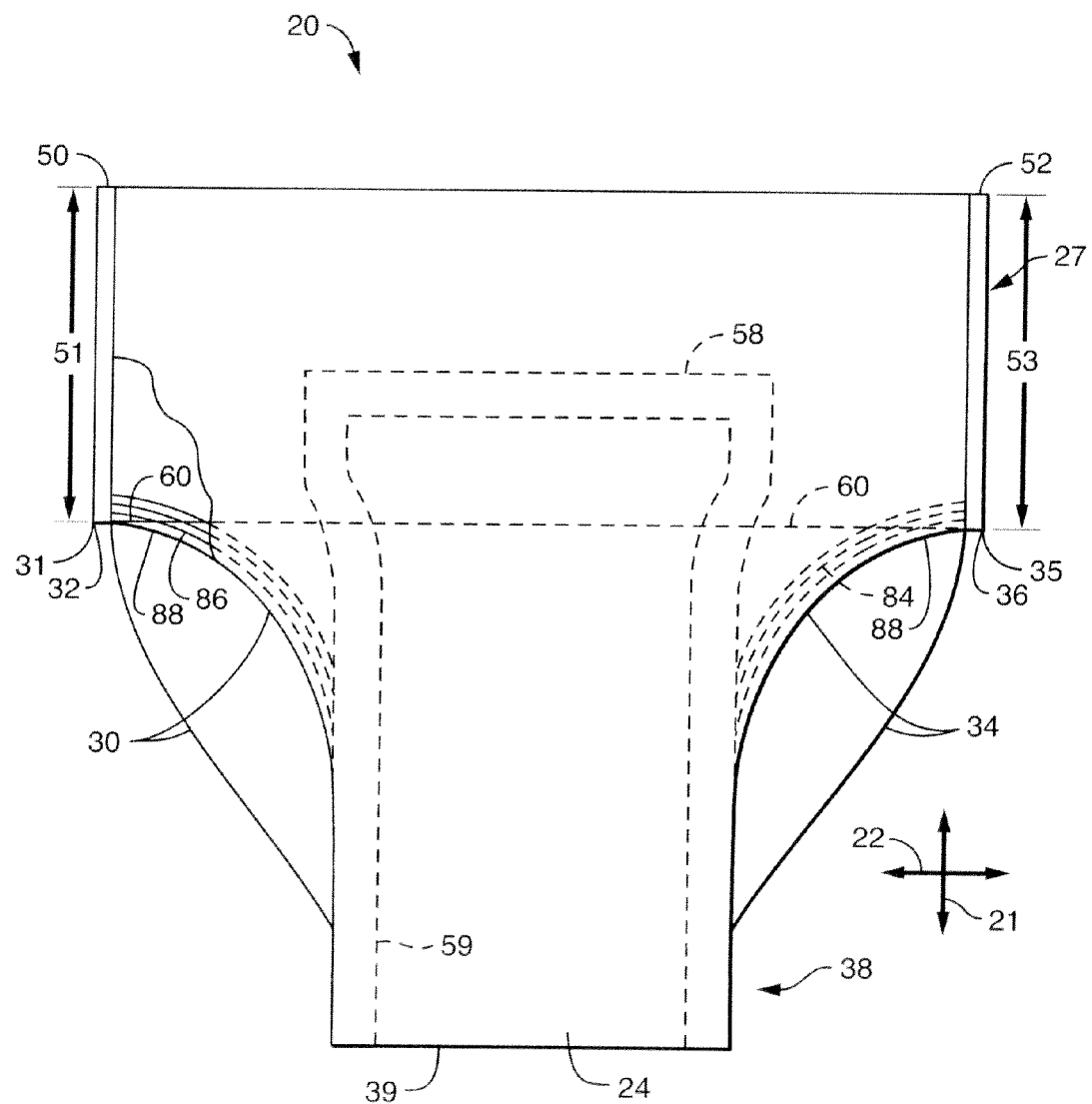
FIG. 9 representatively illustrates a front plan view of an alternative embodiment of a disposable absorbent article incorporating principles of the present invention, shown in a fully assembled, longitudinally stretched, and laid-flat condition, and with portions cut away to show underlying features.

Reference to FIGS. 2-18 shall be made in describing various aspects and embodiments of the invention. It should be noted that the embodiments depicted in FIGS. 2-18 are merely representative examples of the garment and process of the invention. Although for illustrative purposes certain features of the present invention shall be described and illustrated with respect to an adult incontinence garment, the various aspects and embodiments of the present invention are also suitable for use with disposable diapers, disposable swim pants, disposable training pants, disposable enuresis garments, and the like.

Referring to FIGS. 2-10, a particular embodiment of a disposable absorbent garment 20 of the present invention defines a longitudinal direction 21 and a transverse direction 22, and includes a unitary outer cover layer 24. "Unitary" as used herein means formed from an integral piece of material over substantially its entire area, as opposed to being formed from several pieces that are patched together. The unitary outer cover layer 24 defines a front end edge 26, a back end edge 28 longitudinally opposite the front end edge 24, and first and second transversely opposed leg edges 30 and 34 positioned longitudinally between the front end edge 26 and the back end edge 28. The first leg edge 30 defines a front end point 31 and a back end point 32, and the second leg edge 34 defines a front end point 35 and a back end point 36. The outer cover layer 24 defines a front region 27 adjacent the front end edge 26, a back region 29 adjacent the back end edge 28, and a crotch region 38 positioned longitudinally between the front region 27 and back region 29.

The unitary outer cover layer 24 further defines first and second transversely opposed front side edges 40 and 42. The first front side edge 40 extends in the longitudinal direction 21 from the front end edge 26 to the front end point 31 of the first leg edge 30, and the second front side edge 42 extends in the longitudinal direction 21 from the front end edge 26 to the front end point 35 of the second leg edge 34. The unitary outer cover layer 24 also defines first and second transversely opposed back side edges 44 and 46. The first back side edge 44 extends in the longitudinal direction 21 from the back end edge 28 to the back end point 32 of the first leg edge 30, and the second back side edge 46 extends in the longitudinal direction 21 from the back end edge 28 to the back end point 36 of the second leg edge 34.

The garment includes a first side seam 50 at which the first front side edge 40 is attached to the first back side edge 44 and which defines a first side seam length 51. The garment further includes a second side seam 52 at which the second front side edge 42 is attached to the second back side edge 46 and which defines a second side seam length 53.

The garment includes an elastomeric front body panel 60 superposed on and attached to the front region 27 of the outer cover 24. The front body panel 60 comprises an elastomeric film laminate 62 that extends transversely from the first front side edge 40 to the second front side edge 42, that extends longitudinally along the first front side edge 40 a distance at least 50% (for example, FIG. 8), more particularly at least 80%, and still more particularly about 100% (for example, FIG. 10) of the first side seam length 51, and that extends longitudinally along the second front side edge 42 a distance at least 50% (for example, FIG. 8), more particularly at least 80%, and still more particularly about 100% (for example, FIG. 9) of the second side seam length 53. The garment also includes an elastomeric back body panel 70 superposed on and attached to the back region 29 of the outer cover 24. As with the front body panel 60 described above, the back body panel 70 comprises an elastomeric film laminate 72 that extends transversely from the first back side edge 44 to the second back side edge 46, that extends longitudinally along the first back side edge 44 a distance at least 50%, more particularly at least 80%, and still more particularly about 100% of the first side seam length 51, and that extends longitudinally along the second back side edge 46 a distance at least 50%, more particularly at least 80%, and still more particularly about 100% of the second side seam length 53. The garment also includes an absorbent assembly 58 superposed over the crotch region 38 of the outer cover layer 24. The absorbent assembly includes an absorbent core 59, and in particular embodiments includes a bodyside liner 96 and a backsheet 98. U.S. Patent Application Publications US 2008/0095978 and US 2009/0197041, both assigned to Kimberly-Clark Worldwide, Inc., provide examples of technology suitable for use in creating the front and back body panel elastomeric film laminates, although other elastomeric film laminates can also be used.

Figure 10:
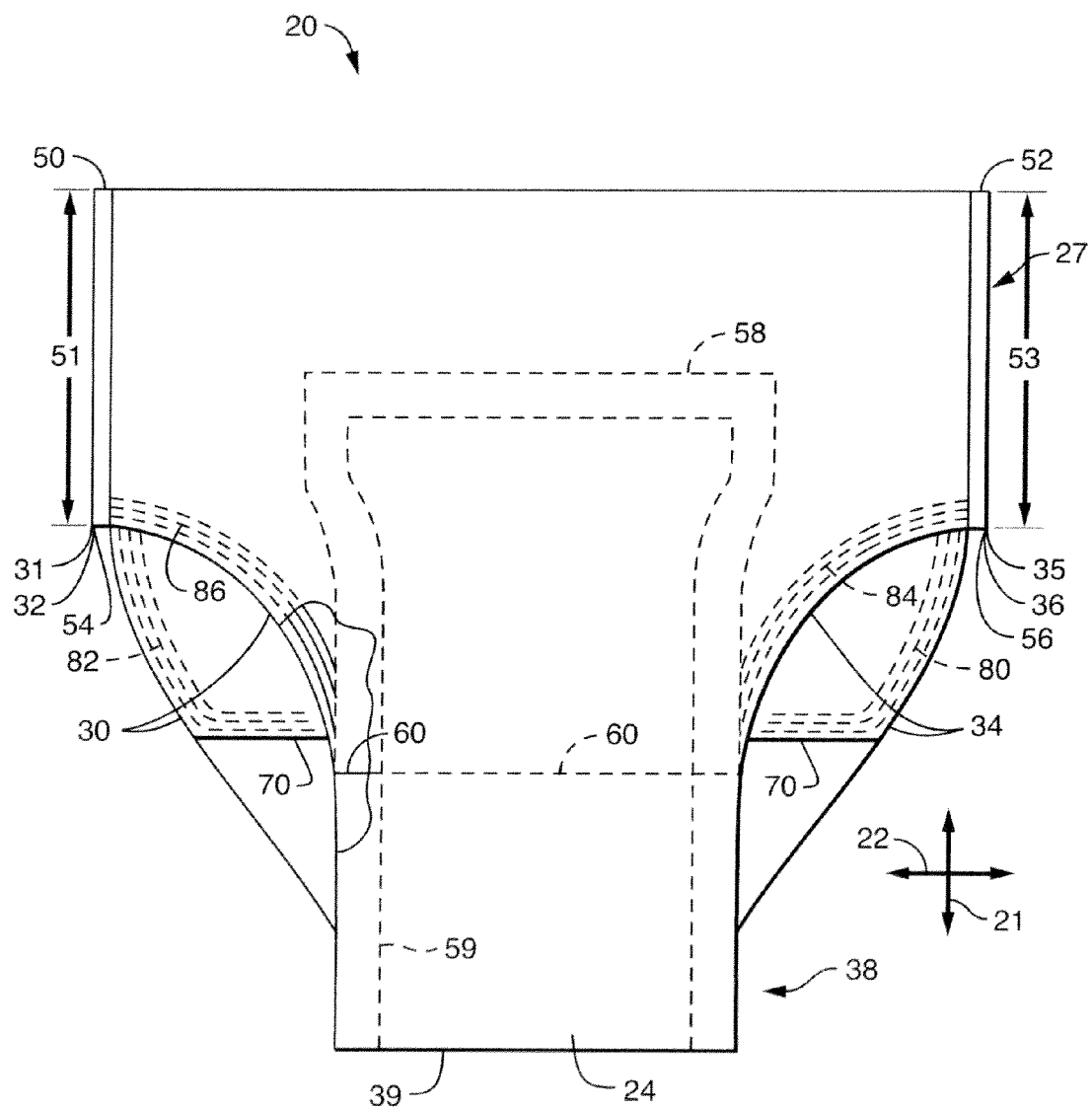
FIG. 10 representatively illustrates a front plan view of an alternative embodiment of a disposable absorbent article incorporating principles of the present invention, shown in a fully assembled, longitudinally stretched, and laid-flat condition, and with portions cut away to show underlying features.
Figure 11:
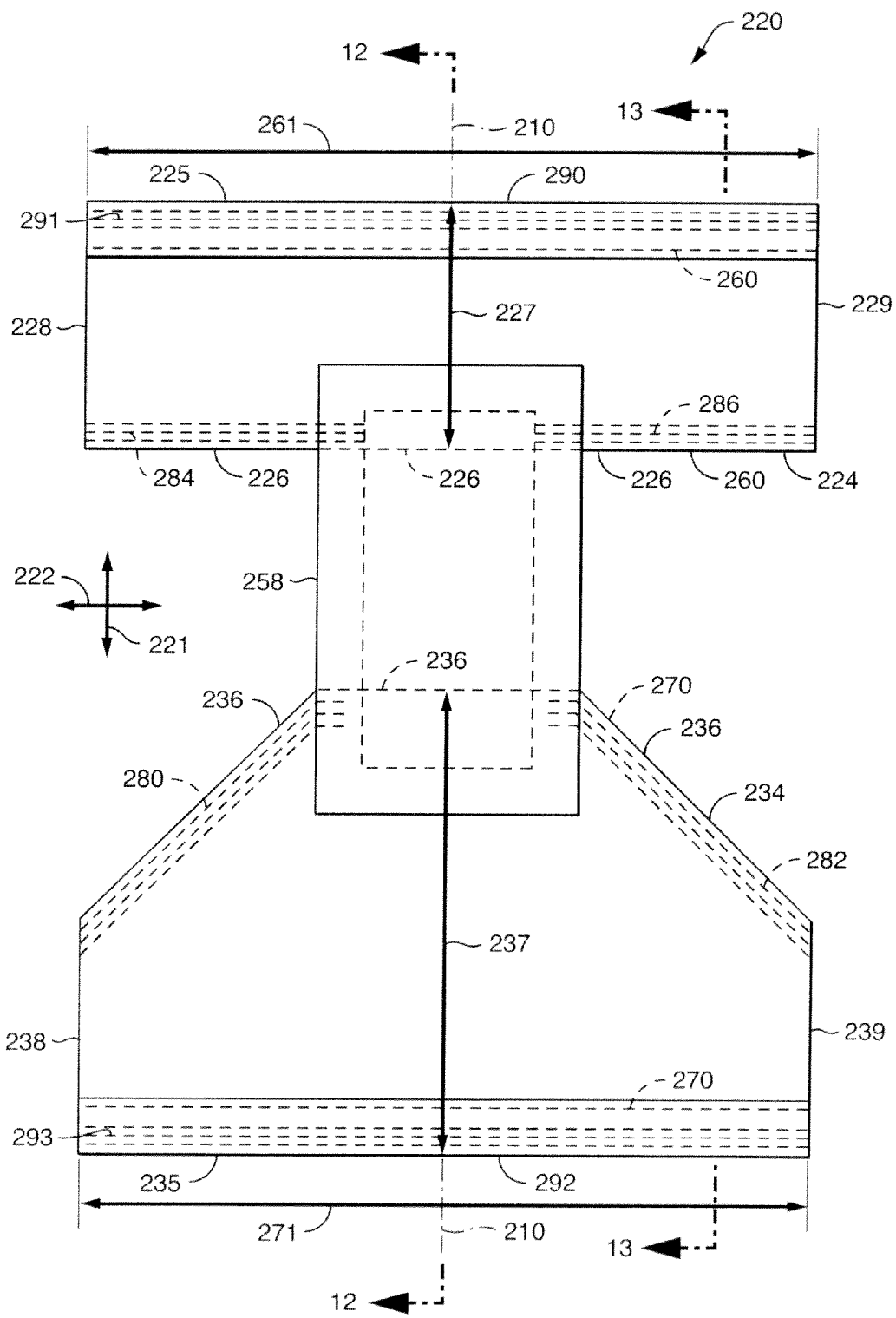
FIG. 11 representatively illustrates a plan view of an alternative embodiment of a disposable absorbent article incorporating principles of the present invention, shown in a longitudinally stretched, and laid-flat condition, prior to the joining of the front and back waist regions, and showing the surface of the article that faces toward the wearer when the article is worn.
Figure 12:
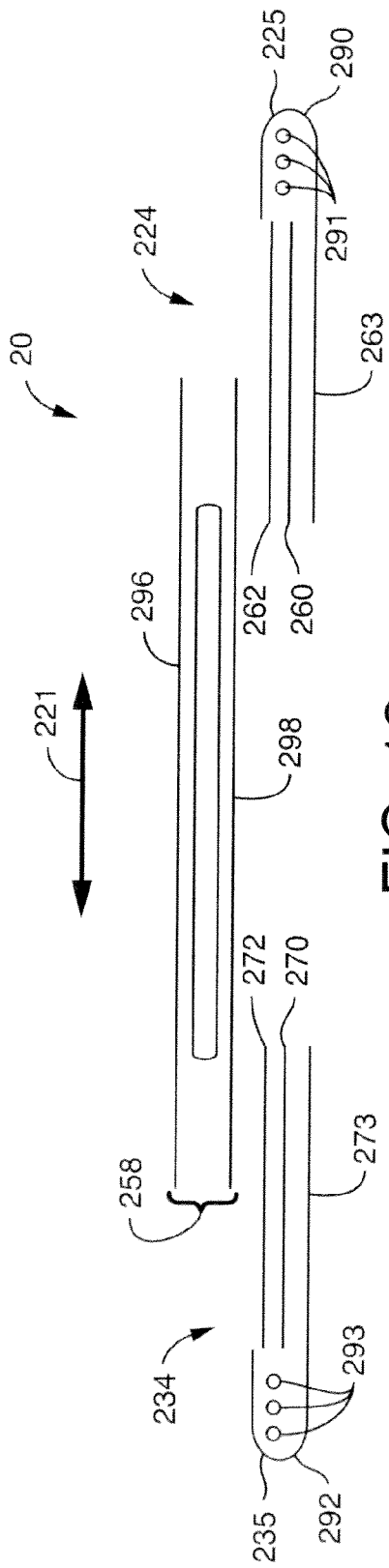
FIG. 12 is a cross-sectional view of the article of FIG. 11 as viewed along line 12-12.
Figure 13:
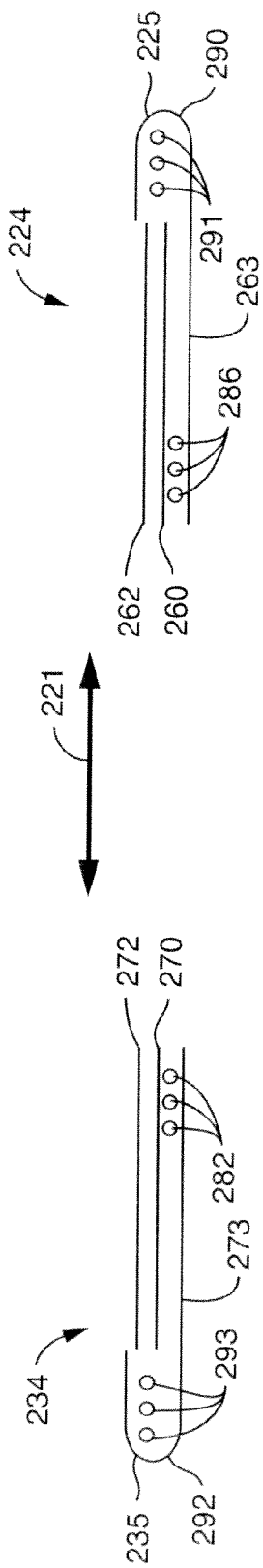
FIG. 13 is a cross-sectional view of the article of FIG. 11 as viewed along line 13-13.
Figure 14:
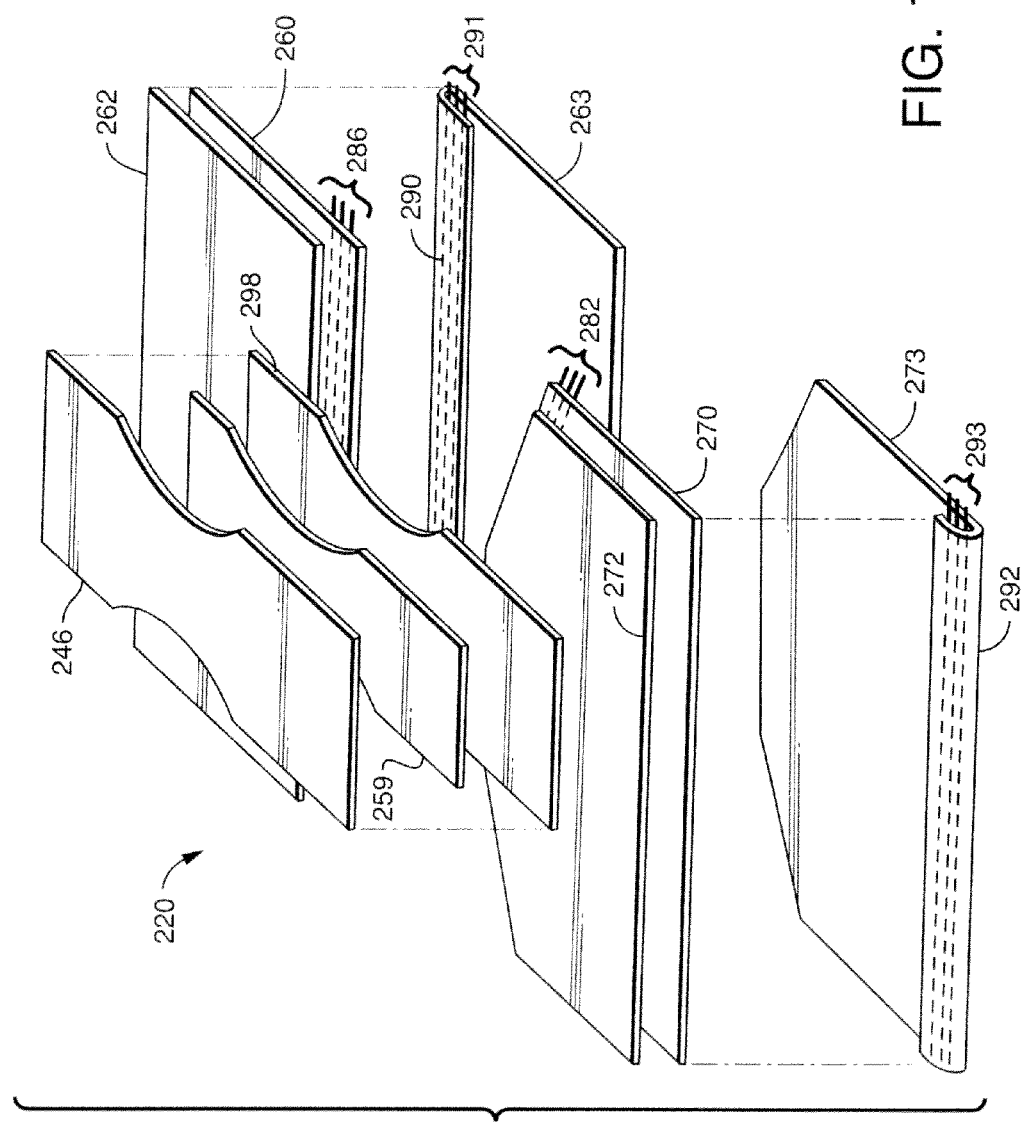
FIG. 14 is an exploded view of the article of FIG. 12, with certain features omitted.
Figure 15:
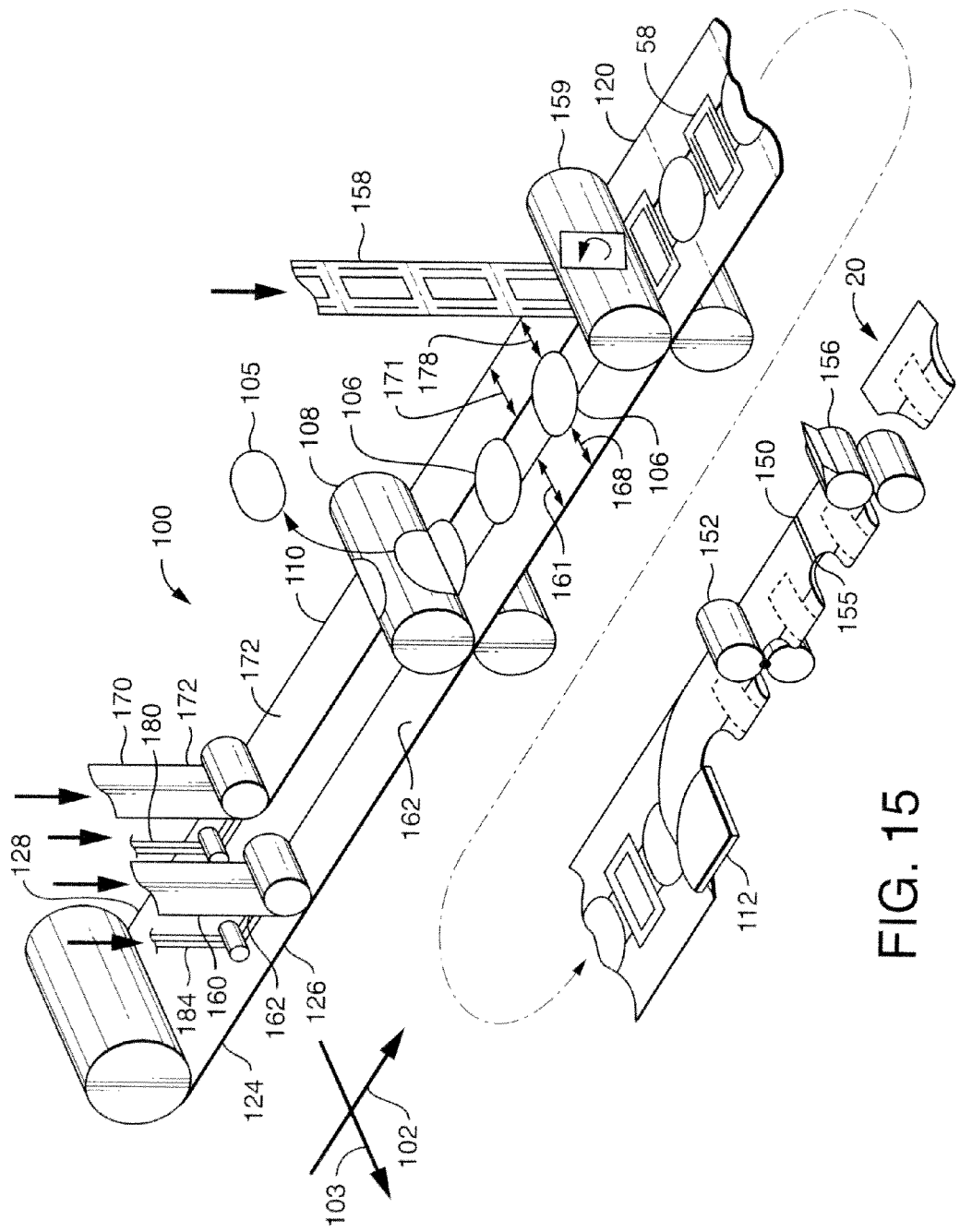
FIG. 15 representatively illustrates a perspective view of one embodiment of a manufacturing process incorporating principles of the process aspect of the present invention.
Figure 16:
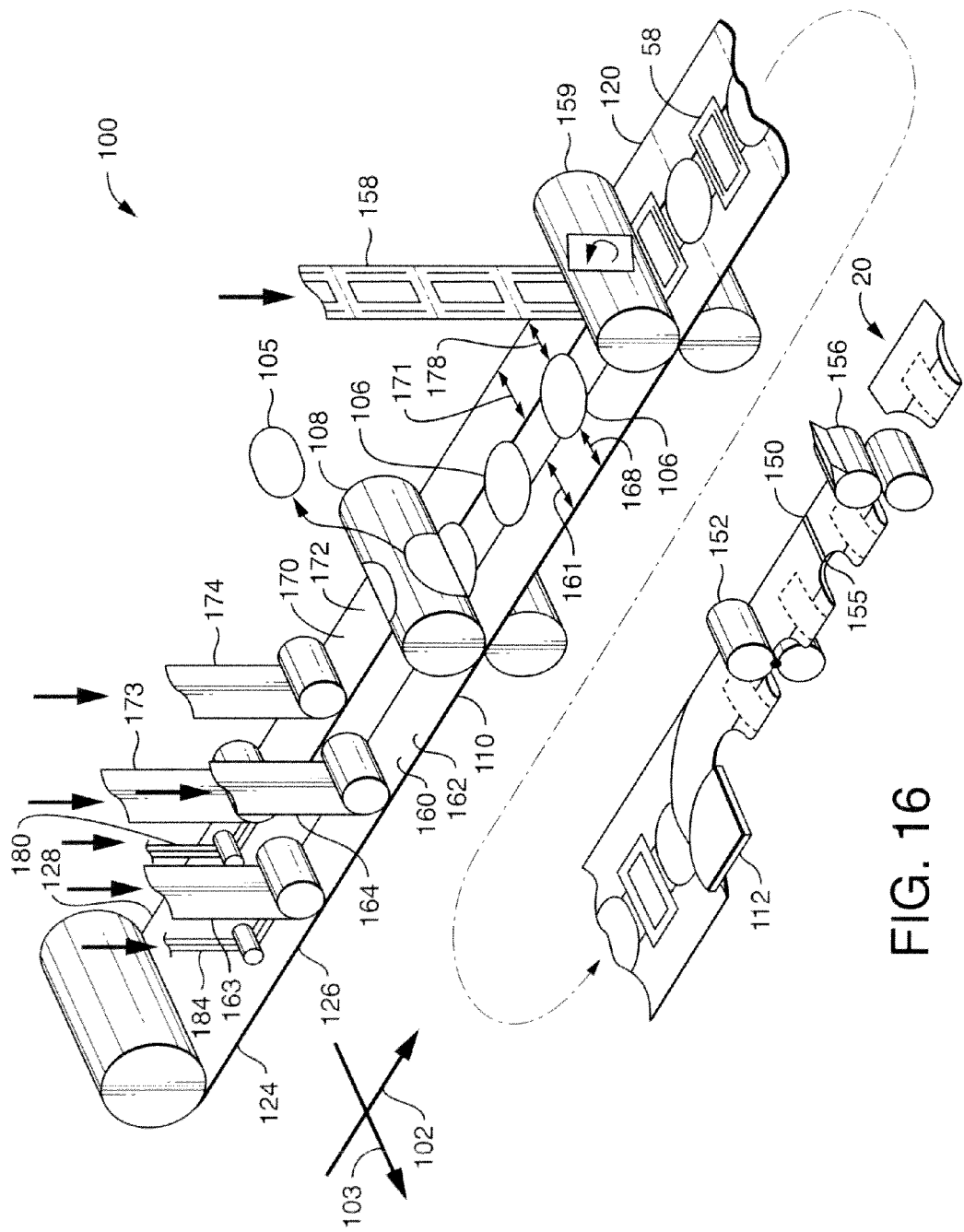
FIG. 16 representatively illustrates a perspective view of an alternative embodiment of a manufacturing process incorporating principles of the process aspect of the present invention.
Figure 17:
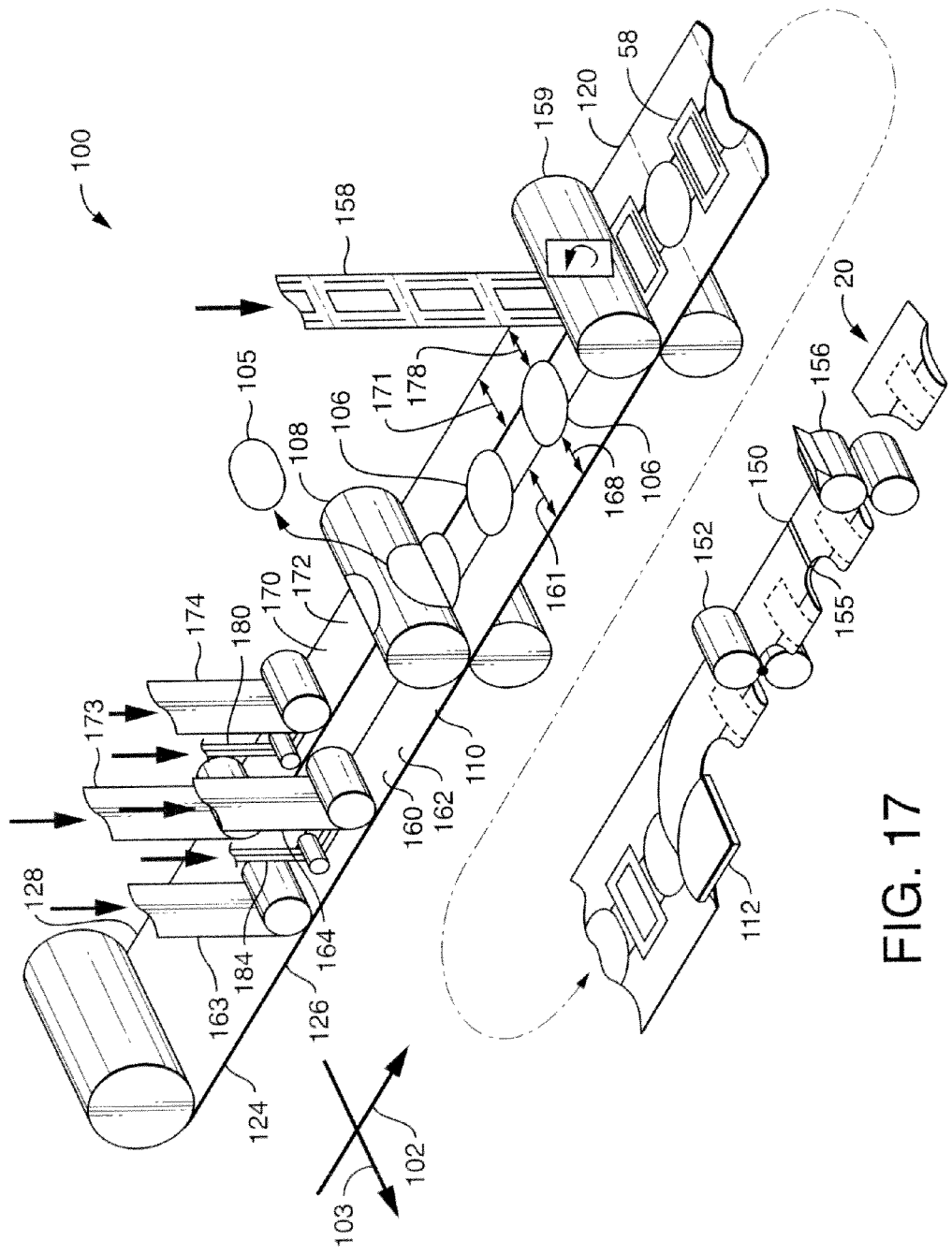
FIG. 17 representatively illustrates a perspective view of another alternative embodiment of a manufacturing process incorporating principles of the process aspect of the present invention.

In certain embodiments, as representatively illustrated in FIG. 10, a portion of the front body panel 60 extends longitudinally inward past both the longitudinally innermost point 54 of the first side seam 50 and the longitudinally innermost point 56 of the second side seam 52. Similarly, in certain embodiments and as representatively illustrated in FIG. 10, a portion of the back body panel 70 extends longitudinally inward past both the longitudinally innermost point 54 of the first side seam and the longitudinally innermost point 56 of the second side seam. "Longitudinally inward" as used herein means in a direction longitudinally toward the central transverse axis 23 (if in a laid flat condition prior to the joining of the front and back regions) or in a direction longitudinally toward the crotch fold 39 (if in a fully assembled condition). "Longitudinally outward" as used herein means in a direction longitudinally away from the central transverse axis 23 (if in a laid flat condition prior to the joining of the front and back regions) or in a direction longitudinally away from the crotch fold 39 (if in a fully assembled condition). "Longitudinally innermost" as used herein means closest to the central transverse axis 23 (if in a laid flat condition prior to the joining of the front and back regions) or closest to the crotch fold 39 (if in a fully assembled condition).

In certain embodiments and as representatively illustrated in FIGS. 3-7, the front body panel 60 is longitudinally spaced from and distinct from the back body panel 70. In particular embodiments, as representatively illustrated in FIGS. 2-4, 6, and 8-10, at least a portion of the absorbent assembly 58 is superposed over a portion of the front body panel 60. Similarly, in particular embodiments and as representatively illustrated in FIGS. 3, 4, and 6, at least a portion of the absorbent assembly 58 is superposed over a portion of the back body panel 70. In such embodiments, it can optionally be the case that a majority of the area of the portion of the front body panel (and/or of the back body panel) superposed by the at least a portion of the absorbent assembly comprises a substantially deadened/inactivated elastomeric film.

In particular embodiments, the elastomeric film laminate 62 in the front body panel 60 comprises a front body panel elastomeric film side or layer 63 and a front body panel nonwoven side or layer 64. Preferably, in such an embodiment, a bodyside surface 65 of the elastomeric film side or layer 63 is directly adhered to the nonwoven layer 64, and a garment-side surface 66 of the elastomeric film side or layer 63 is directly adhered to the unitary outer cover layer 24, as representatively illustrated in FIGS. 3-7. In other embodiments (not shown), a garment-side surface 66 of the elastomeric film side or layer 63 is directly adhered to the nonwoven layer 64, and a bodyside surface 65 of the elastomeric film side or layer 63 is directly adhered to the unitary outer cover layer 24. Similarly, in particular embodiments, the elastomeric film laminate 72 in the back body panel 70 comprises a back body panel elastomeric film side or layer 73 and a back body panel nonwoven side or layer 74. Preferably, in such an embodiment, a bodyside surface 75 of the elastomeric film side layer 73 is directly adhered to the nonwoven layer 74, and a garment-side surface 76 of the elastomeric film side or layer 73 is directly adhered to the unitary outer cover layer 24, as representatively illustrated in FIGS. 3-7. In another embodiment (not shown), a garment-side surface 76 of the elastomeric film side layer 73 is directly adhered to the nonwoven layer 74, and a bodyside surface 75 of the elastomeric film side or layer 73 is directly adhered to the unitary outer cover layer 24.

In particular embodiments, the garment 20 comprises a first back leg elastic member 80 attached to the outer cover layer 24 adjacent at least a portion of the first leg edge 30, and a second back leg elastic member 82 attached to the outer cover layer 24 adjacent at least a portion of the second leg edge 34. In particular embodiments, the garment 20 comprises a first front leg elastic member 84 attached to the outer cover layer 24 adjacent at least a portion of the first leg edge 30, and a second front leg elastic member 86 attached to the outer cover layer 24 adjacent at least a portion of the second leg edge 34. Each leg elastic member 80/82/84/86 can comprise a single strand, ribbon, or strip of elastomeric material, or each can comprise two or more strands, ribbons, or strips, such as, for example, three strands (as depicted in FIGS. 3-10).

In certain embodiments, the first back leg elastic member 80 and the second back leg elastic member 82 are both at least partially sandwiched between the back body panel 70 and the outer cover layer 24. In particular embodiments, as representatively illustrated in FIGS. 3 and 10, the first back leg elastic member 80 and the second back leg elastic member 82 are both entirely sandwiched between the back body panel 70 and the outer cover layer 24. Similarly, in certain embodiments, as representatively illustrated in FIG. 9, the first front leg elastic member 84 and the second front leg elastic member 86 are both at least partially sandwiched between the front body panel 60 and the outer cover layer 24. In particular embodiments, as representatively illustrated in FIGS. 3 and 10, the first front leg elastic member 84 and the second front leg elastic member 86 are both entirely sandwiched between the front body panel 60 and the outer cover layer 24. In embodiments such as those representatively illustrated in FIGS. 8 and 9, in which a leg elastic member (such as front leg elastic members 84 and 86) are not entirely sandwiched between a body panel 60 and the outer cover layer 24, it may be necessary to include a supplemental leg elastic covering layer 88 so that those portions of the leg elastic members 84 and 86 and any concomitant adhesive that are not otherwise fully sandwiched are not exposed. Such a supplemental layer 88 may be formed of suitable nonwoven fabrics as are known in the art.

In certain embodiments, the first back leg elastic member 80 and the second back leg elastic member 82 form part of a single, integral back elastic member 81 that extends from the first back side edge 44 transversely over the absorbent assembly 58 to the second back side edge 46. Similarly, in certain embodiments, the first front leg elastic member 84 and the second front leg elastic member 86 form part of a single, integral front elastic member 85 that extends from the first front side edge 40 transversely over the absorbent assembly 58 to the second front side edge 42.

In particular embodiments, the front body panel 60 defines a front body panel width 61 that extends transversely from the first front side edge 40 to the second front side edge 42, and the front body panel 60 is longitudinally spaced from the front end edge 26 along the entire front body panel width 61. Similarly, in particular embodiments, the back body panel 70 defines a back body panel width 71 that extends transversely from the first back side edge 44 to the second back side edge 46, and the back body panel 70 is longitudinally spaced from the back end edge 28 along the entire back body panel width 71. In certain embodiments, such as those representatively illustrated in FIGS. 3, 4, and 6, the unitary outer cover layer 24 includes a transversely extending front fold 90 that defines the front end edge 26 and a transversely extending back fold 92 that defines the back end edge 28. Such a garment can further include a front waist elastic member 91 positioned within the front fold 90 and a back waist elastic member 93 positioned within the back fold 92. In alternative embodiments, no front waist fold or back waist fold is included; in such embodiments, opposite end edges of the unitary outer cover 24 would define the front end edge 26 of the unitary outer cover 24 and back end edge 28 of the unitary outer cover 24, respectively.

In another aspect, the present invention pertains to a method of manufacturing a plurality of disposable absorbent garments, examples of which are representatively illustrated in FIGS. 15-18. In particular embodiments, the method 100 comprises providing an outer cover web 124 traveling in a machine direction 102. The outer cover web has a front waist edge 126 and a back waist edge 128, both of which extend in the machine direction 102.

The method in particular embodiments further includes providing an elastomeric front body panel web 160 traveling in the machine direction 102, superposing the elastomeric front body panel web 160 on the outer cover web 124, and attaching the front body panel web 160 to the outer cover web 124. The front body panel web 160 comprises an elastomeric film laminate layer 162. In particular embodiments, the elastomeric film laminate layer 162 includes an elastomeric film web layer 163 and a nonwoven web layer 164 that are separately provided and laminated together during the continuous machine manufacture of the garments. For example, as representatively illustrated in FIGS. 16 and 17, the step of providing the elastomeric front body panel web 160 can include providing a roll supply of elastomeric film web layer 163 and providing a separate roll supply of nonwoven web layer 164, superposing the elastomeric film web layer 163 over (or under) the nonwoven web layer 164, and attaching the elastomeric film web layer 163 to the nonwoven web layer 164. In such an embodiment, the step of attaching the elastomeric film web layer 163 to the nonwoven web layer 164 can occur either before or after the composite front body panel web 160 is attached to the outer cover web 124. In alternative embodiments, the elastomeric film laminate 162 includes an elastomeric film web layer 163 and a nonwoven web layer 164 that are laminated together prior to being fed into the continuous machine manufacture of the garments. For example, as representatively illustrated in FIGS. 15 and 18, the step of providing the elastomeric front body panel web 160 can include providing a single roll supply of elastomeric film laminate, wherein the laminate on the single roll supply comprises at least two layers, one layer being an elastomeric film web layer 163 and the other layer being a nonwoven layer 164. Note that in FIGS. 15 and 18, individual layers of the elastomeric film laminate 162 are not depicted, but instead the laminate is depicted as a single, "pre-made" laminate substrate. In particular embodiments, the front body panel web 160 comprises an elastomeric film layer 162 and a nonwoven layer 164, and the attaching of the front body panel web 160 to the outer cover web 124 comprises adhering the elastomeric film layer 162 of the front body panel web 160 directly to the outer cover web 124, meaning that there are no intervening sheets or films (other than a bonding agent, such as adhesive).

Similarly, the method in particular embodiments further includes providing an elastomeric back body panel web 170 traveling in the machine direction 102, superposing the elastomeric back body panel web 170 on the outer cover web 124, and attaching the back body panel web 170 to the outer cover web 124. The back body panel web 170 comprises an elastomeric film laminate layer 172. In particular embodiments, the elastomeric film laminate 172 includes an elastomeric film web layer 173 and a nonwoven web layer 174 that are separately provided and laminated together during the continuous machine manufacture of the garments. For example, as representatively illustrated in FIGS. 16 and 17, the step of providing the elastomeric back body panel web 170 can include providing a roll supply of elastomeric film web layer 173 and providing a separate roll supply of nonwoven web layer 174, superposing the elastomeric film web layer 173 over (or under) the nonwoven web layer 174, and attaching the elastomeric film web layer 173 to the nonwoven web layer 174. In such an embodiment, the step of attaching the elastomeric film web layer 173 to the nonwoven web layer 174 can occur either before or after the back body panel web 170 is attached to the outer cover web 124. In alternative embodiments, the elastomeric film laminate 172 includes an elastomeric film web layer 173 and a nonwoven web layer 174 that are laminated together prior to being fed into the continuous machine manufacture of the garments. For example, as representatively illustrated in FIGS. 15 and 18, the step of providing the elastomeric back body panel web 170 can include providing a single roll supply of elastomeric film laminate, wherein the laminate on the single roll supply comprises at least two layers, one layer being an elastomeric film web layer 173 and the other layer being a nonwoven layer 174. Note that in FIGS. 15 and 18, individual layers of the elastomeric film laminate 172 are not depicted, but instead the laminate is depicted as a single, "pre-made" laminate substrate. In particular embodiments, the back body panel web 170 comprises an elastomeric film layer 172 and a nonwoven layer 174, and the attaching of the back body panel web 170 to the outer cover web 124 comprises adhering the elastomeric film layer 172 of the back body panel web 170 directly to the outer cover web 124, meaning that there are no intervening sheets or films (other than a bonding agent, such as adhesive).

The outer cover web 124, the front body panel web 160, and the back body panel web 170 collectively define a composite garment web 110. The method in particular embodiments further includes providing a supply 158 of individual absorbent assemblies 58, superposing individual absorbent assemblies 58 over the composite garment web 110, and attaching the individual absorbent assemblies 58 to the composite garment web 110. In certain embodiments, such as those representatively illustrated in FIGS. 15-18, the absorbent articles may be manufactured in one orientation, and then cut and rotated 90 degrees (such as at cut-and-rotate station 159) before attachment to the composite garment web 110. The method can in particular embodiments further include removing portions 105 of the outer cover web 124 (such as at cutting station 108) to define a series of spaced apart holes 106, thereby defining in the composite garment web 110 a interconnected series 120 of disposable absorbent garments 20. Such portions 105 can be removed from the outer cover web 124 before the front body panel web 160 and/or back body panel web 170 are attached to the outer cover web 124 (not shown), or can be removed from the outer cover web 124 after the front body panel web 160 and/or back body panel web 170 are attached to the outer cover web 124 (as representatively illustrated in FIGS. 15-18). Furthermore, such portions 105 can be removed from the outer cover web 124 before the individual absorbent assemblies 58 are attached to the outer cover web 124 (as representatively illustrated in FIGS. 15-18), or can be removed from the outer cover web 124 after the individual absorbent assemblies 58 are attached to the outer cover web 124 (not shown).

The elastomeric front body panel web 160 defines a front body panel web width 161 that extends in a cross-machine direction 103. The front body panel web width 161 extends at least 50%, more particularly at least 70%, still more particularly at least 90%, and yet still more particularly at least 100% of a shortest distance 168 extending from the front waist edge 126 to each hole 106. In one preferred embodiment, such as those representatively illustrated in FIGS. 15-18, the front body panel web width 161 exceeds the shortest distance 168 extending from the front waist edge 126 to each hole 106. As the front body panel web width 161 is increased, the resulting garment becomes better elasticized and more underwear-like. In particular embodiments, such as that representatively illustrated in FIGS. 15-18, at least a portion of each individual absorbent assembly 58 overlays at least a portion of the elastomeric front body panel web 160.

The elastomeric back body panel web 170 defines a back body panel web width 171 that extends in the cross-machine direction 103. The back body panel web width 171 extends at least 50%, more particularly at least 70%, still more particularly at least 90%, and yet still more particularly at least 100% of a shortest distance 178 extending from the back waist edge 128 to each hole 106. In one preferred embodiment, as representatively illustrated in FIGS. 15-18, the back body panel web width 171 exceeds the shortest distance 178 extending from the back waist edge 128 to each hole 106. As the back body panel web width 171 is increased, the resulting garment becomes better elasticized and more underwear-like. In particular embodiments, such as that representatively illustrated in FIGS. 15-18, at least a portion of each individual absorbent assembly 58 overlays at least a portion of the elastomeric back body panel web 170.

In particular embodiments, such as that representatively illustrated in FIGS. 15-18, after attaching the front body panel web 160 to the outer cover web 124 and after attaching the back body panel web 170 to the outer cover web 124, the front body panel web 160 is spaced in the cross-machine direction 103 apart from the back body panel web 170. In other embodiments, after attaching the front body panel web 160 to the outer cover web 124 and after attaching the back body panel web 170 to the outer cover web 124, the front body panel web 160 can abut or even overlap the back body panel web 170.

The method 100 can further include folding the composite garment web 110, such as at a garment folding station 112, along a transversely centered longitudinal fold line that extends in the machine direction 102, such that the front waist edge 126 is brought into close proximity with the back waist edge 128. In particular embodiments, the method further comprises attaching the front body panel web 160 to the back body panel web 170 to create a series of side seam bonds 150 (such as at seaming station 152) spaced apart in the machine direction 102. The method additionally comprises cutting the composite garment web 110 at a series of cut locations 155 (such as at cutting station 156) spaced apart in the machine direction 102 to create the plurality of disposable absorbent garments.

In particular embodiments, the method 100 also includes attaching a continuous back leg elastic member 180 to the outer cover web 124. The back leg elastic member 180 extends or travels predominantly in the machine direction 102. In particular embodiments, as representatively illustrated in FIGS. 15-18, the method further comprises at least partially overlapping the back leg elastic member 180 with the elastomeric back body panel web 170. For example, the method may comprise sandwiching at least a portion of the continuous back leg elastic member 180 between the back body panel web 170 and the outer cover web 124. Similarly, in particular embodiments, the method 100 also includes attaching a continuous front leg elastic member 184 to the outer cover web 124. The front leg elastic member 184 extends or travels predominantly in the machine direction 102. In particular embodiments, as representatively illustrated in FIGS. 15-18, the method further comprises at least partially overlapping the front leg elastic member 184 with the elastomeric front body panel web 160. For example, the method may comprise sandwiching at least a portion of the continuous front leg elastic member 184 between the front body panel web 160 and the outer cover web 124. In certain embodiments, the method 100 further comprises cutting the continuous back leg elastic member 180 and/or the continuous front leg elastic member 184 at a series of elastic cut points spaced apart in the machine direction, each elastic cut point being generally aligned in the machine direction 102 with a respective individual absorbent assembly 58 (not shown). Suitable methods for such cutting step are disclosed in U.S. Pat. No. 5,660,657 issued May 5, 1998 to Rajala et al. and assigned to Kimberly-Clark Worldwide, Inc., the entirety of which is incorporated herein by reference to the extent consistent herewith.

Figure 18:
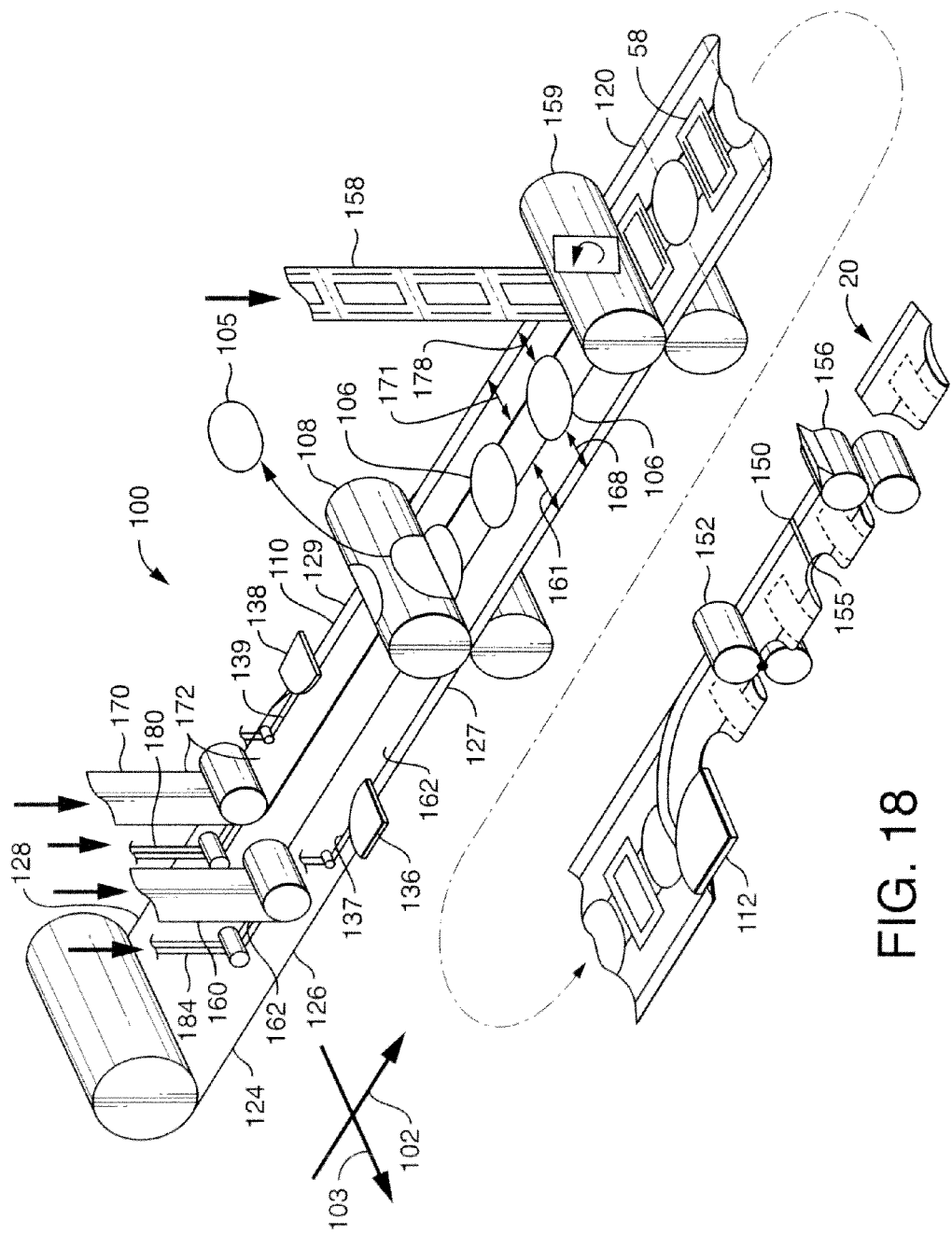
FIG. 18 representatively illustrates a perspective view of yet another alternative embodiment of a manufacturing process incorporating principles of the process aspect of the present invention.

In particular embodiments, such as that representatively illustrated in FIG. 18, the method further includes folding the front waist edge 126 of the outer cover web 124, such as at a front waistband folding station 136, to create a front waist edge fold 127 and to encase a front waist elastic member 137. In such an embodiment, the front waist edge fold 127 defines the front waist edge 126 of the outer cover web 124. The method may instead or additionally include folding the back waist edge 128 of the outer cover web 124, such as at back waistband folding station 138, to create a back waist edge fold 129 and to encase a back waist elastic member 139. In such an embodiment, the back waist edge fold 129 defines the back waist edge 128 of the outer cover web 124. Note that in such an embodiment, the front body panel web width 161 and the back body panel width 171 are measured after the creation of the front and back waist edge folds 127/129, as illustrated in FIG. 18.

In particular embodiments, various components, such as the outer cover web 124, one or more layers of the front body panel web 160, and/or one or more layers of the back body panel web 170, can be printed or pigmented to include graphics, text, color, or other images. Such printing can occur during assembly of the garment in conjunction with the presently disclosed method, or can occur prior to such assembly in an off-line, "pre-preprinting" or pigmenting step.

Referring to FIGS. 11-14, an alternative embodiment of the garment aspect of the present invention shall now be described. In this embodiment, a disposable absorbent garment 220 defines a longitudinal direction 221 and a transverse direction 222. The garment 220 comprises a front panel 224 which defines a front panel end edge 225, a front panel crotch edge 226 longitudinally opposite the front panel end edge 225, a front panel length 227 extending longitudinally from the front panel end edge 225 to the front panel crotch edge 226 and measured at the longitudinal centerline 210 of the garment 220, and first and second transversely opposed front panel side edges 228 and 229. The first front panel side edge 228 extends in the longitudinal direction 221 from the front panel end edge 225 to the front panel crotch edge 226, and the second front panel side edge 229 extends in the longitudinal direction 221 from the front panel end edge 225 to the front panel crotch edge 226. The front panel 224 comprises a front panel elastomeric film 260 which extends transversely from the first front panel side edge 228 to the second front panel side edge 229. The front panel 224 can further comprise a front panel inner nonwoven layer 262 and a front panel outer nonwoven layer 263. The front panel elastomeric film 260 extends longitudinally at least 70%, more particularly at least 80%, and still more particularly at least 95% of the front panel length 227.

The garment 220 further comprises a back panel 234 which defines a back panel end edge 235, a back panel crotch edge 236 longitudinally opposite the back panel end edge 235, a back panel length 237 extending longitudinally from the back panel end edge 235 to the back panel crotch edge 236 and measured at the longitudinal centerline 210 of the garment 220, and first and second transversely opposed back panel side edges 238 and 239. The first back panel side edge 238 extends in the longitudinal direction 221 from the back panel end edge 235 to the back panel crotch edge 236, and the second back panel side edge 239 extends in the longitudinal direction 221 from the back panel end edge 235 to the back panel crotch edge 236. The back panel 234 comprises a back panel elastomeric film 270 which extends transversely from the first back panel side edge 238 to the second back panel side edge 239. The back panel 234 can further comprise a back panel inner nonwoven layer 272 and a back panel outer nonwoven layer 273. The back panel elastomeric film 270 extends longitudinally at least 70%, more particularly at least 80%, and still more particularly at least 95% of the back panel length 237.

The back panel 234 may include first and second back leg elastic members 280 and 282, each of which extends along at least a portion of the back panel crotch edge 236. Each back leg elastic member 280 and 282 at least partially overlaps the back panel elastomeric film 270. In a particular embodiment, both the first back leg elastic member 280 and the second back leg elastic member 282 are both entirely overlapped by the back panel elastomeric film 270. For example, both the first back leg elastic member 280 and the second back leg elastic member 282 may each be entirely sandwiched between the back panel elastomeric film 270 and a nonwoven facing affixed to the back panel elastomeric film 270.

Similarly, the front panel 224 may include first and second front leg elastic members 284 and 286, each of which extends along at least a portion of the front panel crotch edge 226. In this particular embodiment, each front leg elastic member 284 and 286 at least partially overlaps the front panel elastomeric film 260. In a particular embodiment, both the first front leg elastic member 284 and the second front leg elastic member 286 are both entirely overlapped by the front panel elastomeric film 260. For example, both the first front leg elastic member 284 and the second front leg elastic member 286 may each be entirely sandwiched between the front panel elastomeric film 260 and a nonwoven facing affixed to the front panel elastomeric film 260. Each leg elastic member 280/282/284/286 can comprise a single strand, ribbon, or strip of elastomeric material, or each can comprise two or more strands, ribbons, or strips, such as, for example, three strands (as depicted in FIGS. 11-14).

The garment 220 further comprises an absorbent assembly 258 that extends between and interconnects the front panel 224 and the back panel 234. The absorbent assembly can include an absorbent core 259, a liner 296, and a backsheet 298. In particular embodiments, at least a portion of the absorbent assembly 258 is superposed over a portion of the front panel 224. In additional or in the alternative, at least a portion of the absorbent assembly 258 may be superposed over a portion of the back panel 234. In particular embodiments, a majority of the area of the portion of the front panel superposed by the at least a portion of the absorbent assembly comprises a deadened elastomeric film. Suitable configurations for such deadened/deactivated/inactive elastomeric regions are disclosed in U.S. patent application Ser. No. 12/346,060, entitled "Disposable Absorbent Garments Employing Elastomeric Film Laminates With Deactivated Regions" and filed Dec. 30, 2008 in the name of Stabelfeldt et al. and assigned to Kimberly-Clark Worldwide, Inc., the entirety of which is incorporated herein by reference to the extent consistent herewith. In particular embodiments, the first back leg elastic 280 and the second back leg elastic 282 may form part of a single, integral back elastic that extends transversely over the absorbent assembly 258. In addition or instead, the first front leg elastic 284 and the second front leg elastic 286 may form part of a single, integral front elastic that extends transversely over the absorbent assembly 258. In other embodiments, such as those depicted in FIGS. 11-14, the first back leg elastic 280 and the second back leg elastic 282 are disconnected and transversely spaced from each other, such that no back leg elastic component extends transversely over the absorbent assembly 258. In addition or instead, such as is depicted in FIGS. 11-14, the first front leg elastic 284 and the second front leg elastic 286 are disconnected and transversely spaced from each other, such that no front leg elastic component extends transversely over the absorbent assembly 258.

In particular embodiments, the front panel elastomeric film 260 defines a front panel elastomeric film width 261, measured at the front panel end edge 225, that extends transversely from the first front panel side edge 228 to the second front panel side edge 229. The front panel elastomeric film 260 can be longitudinally spaced from the front panel end edge 225 along the entire front panel elastomeric film width 261. In such embodiments, the front panel can but need not include a transversely extending front fold 290 that defines the front panel end edge 225, and can include a front waist elastic member 291 positioned within the front fold 290.

Additionally or alternatively, the back panel elastomeric film 270 defines a back panel elastomeric film width 271, measured at the back panel end edge 235, that extends transversely from the first back panel side edge 238 to the second back panel side edge 239. The back panel elastomeric film 270 can be longitudinally spaced from the back panel end edge 235 along the entire back panel elastomeric film width 271. In such embodiments, the back panel can but need not include a transversely extending back fold 292 that defines the back panel end edge 235, and can include a back waist elastic member 293 positioned within the back fold 292. The garment 220 can further include a first side seam at which the first front panel side edge 228 is attached to the first back panel side edge 238, as well as a second side seam at which the second front panel side edge 229 is attached to the second back panel side edge 239.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

I claim:

1. A method of manufacturing a plurality of disposable absorbent garments comprising:

providing a unitary outer cover web traveling in a machine direction, the unitary outer cover web having a front waist edge and a back waist edge, both the front waist edge and the back waist edge extending in the machine direction;

providing an elastomeric front body panel web traveling in the machine direction, superposing the elastomeric front body panel web on the unitary outer cover web, and attaching the front body panel web to the unitary outer cover web, the front body panel web comprising an elastomeric film laminate;

providing an elastomeric back body panel web traveling in the machine direction, superposing the elastomeric back body panel web on the unitary outer cover web, and attaching the back body panel web to the unitary outer cover web, the back body panel web comprising an elastomeric film laminate, the unitary outer cover web, the front body panel web, and the back body panel web collectively defining a composite garment web;

further comprising attaching a front leg elastic member to the unitary outer cover web, the front leg elastic member traveling predominantly in the machine direction; and further comprising at least partially overlapping the front leg elastic member with the elastomeric front body panel web;

further comprising attaching a continuous back leg elastic member to the unitary outer cover web, the back leg elastic member traveling predominantly in the machine direction; and further comprising at least partially overlapping the back leg elastic member with the elastomeric back body panel web;

providing a supply of individual absorbent assemblies, superposing individual absorbent assemblies over the composite garment web, and attaching the individual absorbent assemblies to the composite garment web wherein at least a portion of each individual absorbent assembly overlays at least a portion of the elastomeric front body panel web such that the portion of the elastomeric front body panel web is positioned between the portion of the individual absorbent assembly and the unitary outer cover web and wherein at least a portion of each individual absorbent assembly overlays at least a portion of the elastomeric back body panel web such that the portion of the elastomeric back body panel web is positioned between the portion of the individual absorbent assembly and the unitary outer cover web;

removing portions of the unitary outer cover web to define a series of spaced apart holes, thereby defining in the composite garment web a series of interconnected disposable absorbent garments, wherein the elastomeric front body panel web defines a front body panel web width that extends in a cross-machine direction, the front body panel web width exceeds a shortest distance extending from the front waist edge to each hole; and wherein the elastomeric back body panel web defines a back body panel width that extends in a cross-machine direction, the back body panel web width exceeds a shortest distance extending from the back waist edge to each hole;

folding the composite garment web along a central fold line that extends in the machine direction, such that the front waist edge is brought into close proximity with the back waist edge;

attaching the front body panel web to the back body panel web to create a series of side seam bonds spaced apart in the machine direction; and cutting the composite garment web at a series of cut locations spaced apart in the machine direction to create the plurality of disposable absorbent garments.

2. The method of claim 1 further comprising sandwiching at least a portion of the continuous back leg elastic member between the back body panel web and the outer cover web.

3. The method of claim 1 further comprising cutting the continuous back leg elastic member at a series of elastic cut points spaced apart in the machine direction, each elastic cut point being generally aligned in the machine direction with a respective individual absorbent assembly.

4. The method of claim 1 wherein the front body panel web comprises an elastomeric film layer and a nonwoven layer, wherein attaching the front body panel web to the outer cover web comprises adhering the elastomeric film layer of the front body panel web directly to the outer cover web; and wherein the back body panel web comprises an elastomeric film layer and a nonwoven layer, wherein attaching the back body panel web to the outer cover web comprises adhering the elastomeric film layer of the back body panel web directly to the outer cover web.

5. The method of claim 1 wherein the majority of the area of the portion of the front body panel superposed by the at least a portion of the absorbent assembly comprises a substantially deadened elastomeric film.

6. The method of claim 1 wherein, after attaching the front body panel web to the outer cover web and after attaching the back body panel web to the outer cover web, the front body panel web is spaced in the cross-machine direction apart from the back body panel web by the crotch region.

7. The method of claim 1 further comprising folding the front waist edge of the outer cover web to encase a front waist elastic member and folding the back waist edge of the outer cover web to encase a back waist elastic member.

8. A method of manufacturing a plurality of disposable absorbent garments comprising:

providing a unitary outer cover web traveling in a machine direction, the unitary outer cover web having a front waist edge and a back waist edge, both the front waist edge and the back waist edge extending in the machine direction;

attaching a continuous front leg elastic member to the unitary outer cover web, the front leg elastic member traveling predominantly in the machine direction;

attaching a continuous back leg elastic member to the unitary outer cover web, the back leg elastic member traveling predominantly in the machine direction;

providing an elastomeric front body panel web traveling in the machine direction, superposing the elastomeric front body panel web on the unitary outer cover web, and attaching the front body panel web to the unitary outer cover web, the front body panel web comprising an elastomeric film laminate;

providing an elastomeric back body panel web traveling in the machine direction, superposing the elastomeric back body panel web on the unitary outer cover web, and attaching the back body panel web to the unitary outer cover web, the back body panel web comprising an elastomeric film laminate;

wherein the front body panel web comprises an elastomeric film layer and a nonwoven layer, and wherein attaching the front body panel web to the unitary outer cover web comprises adhering the elastomeric film layer of the front body panel web directly to the unitary outer cover web; and wherein the back body panel web comprises an elastomeric film layer and a nonwoven layer, and wherein attaching the back body panel web to the unitary outer cover web comprises adhering the elastomeric film layer of the back body panel web directly to the unitary outer cover web; and wherein, after attaching the front body panel web to the unitary outer cover web and after attaching the back body panel web to the unitary outer cover web, the front body panel web is spaced in the cross-machine direction apart from the back body panel web;

wherein the unitary outer cover web, the front body panel web, and the back body panel web collectively define a composite garment web;

providing a supply of individual absorbent assemblies, superposing individual absorbent assemblies over the composite garment web, and attaching the individual absorbent assemblies to the composite garment web, wherein at least a portion of each individual absorbent assembly overlays at least a portion of the elastomeric front body panel web such that the portion of the elastomeric front body panel web is positioned between the portion of the individual absorbent assembly and the unitary outer cover web and wherein at least a portion of each individual absorbent assembly overlays at least a portion of the elastomeric back body panel web such that the portion of the elastomeric back body panel web is positioned between the portion of the individual absorbent assembly and the unitary outer cover web;

removing portions of the unitary outer cover web to define a series of spaced apart holes, thereby defining in the composite garment web a series of interconnected disposable absorbent garments, wherein the elastomeric front body panel web defines a front body panel web width that extends in a cross-machine direction, the front body panel web width extending at least 90% of a shortest distance extending from the front waist edge to each hole; and wherein the elastomeric back body panel web defines a back body panel width that extends in a cross-machine direction, the back body panel web width extending at least 90% of a shortest distance extending from the back waist edge to each hole;

folding the composite garment web along a central fold line that extends in the machine direction, such that the front waist edge is brought into close proximity with the back waist edge;

attaching the front body panel web to the back body panel web to create a series of side seam bonds spaced apart in the machine direction; and cutting the composite garment web at a series of cut locations spaced apart in the machine direction to create the plurality of disposable absorbent garments.

9. The method of claim 8 further comprising at least partially overlapping the front leg elastic member with the elastomeric front body panel web, and further comprising at least partially overlapping the back leg elastic member with the elastomeric back body panel web.

10. The method of claim 8 further comprising sandwiching at least a portion of the continuous back leg elastic member between the back body panel web and the outer cover web.

11. The method of claim 8 wherein the front body panel web width exceeds the shortest distance extending from the front waist edge to each hole, and wherein the back body panel web width exceeds the shortest distance extending from the back waist edge to each hole.

12. The method of claim 8 wherein the majority of the area of the portion of the front body panel superposed by the at least a portion of the absorbent assembly comprises a substantially deadened elastomeric film.

\* \* \* \* \*